United States Patent [19]

Economides et al.

[11] Patent Number: 6,075,007

[45] Date of Patent: Jun. 13, 2000

[54] MODIFIED NOGGIN POLYPEPTIDE AND COMPOSITIONS

[75] Inventors: Aris Economides, New York; Neil E. Stahl, Carmel, both of N.Y.; Richard M. Harland, Moraga, Calif.

[73] Assignees: Regeneron Pharmaceuticals, Inc., Tarrytown, N.Y.; Regents of the Univ. of California, Oakland, Calif.

[21] Appl. No.: 08/897,236

[22] Filed: Jul. 17, 1997

[51] Int. Cl.7 .............................. A61K 38/16; C07K 14/00
[52] U.S. Cl. .............................. 514/12; 530/397; 530/399
[58] Field of Search ................................ 530/350, 397, 530/399; 514/2, 12

[56] References Cited

U.S. PATENT DOCUMENTS 5,670,481 9/1997 Harland et al. .
5,821,124 10/1998 Valenzuela et al. .
5,843,775 12/1998 Valenzuela et al. .

*Primary Examiner*—Elizabeth Kemmerer
*Attorney, Agent, or Firm*—Robert J. Cobert

[57] ABSTRACT

Described are modified Noggin muteins, compositions comprising the muteins, and DNA or RNA sequences comprising coding (sense) or antisense sequences for the muteins.

6 Claims, 20 Drawing Sheets

Fig. 1A

```
         10              20              30              40
          *               *               *               *
ATG GAG CGC TGC CCC AGC CTA GGG GTC ACC CTC TAC GCC CTG GTG
 M   E   R   C   P   S   L   G   V   T   L   Y   A   L   V>

50              60              70              80              90
      *               *               *               *               *
GTG GTC CTG GGC CTG CGG GCG ACA CCG GCC GGC GGC CAG CAC TAT
 V   V   L   G   L   R   A   T   P   A   G   G   Q   H   Y>

100             110             120             130
          *               *               *               *
CTC CAC ATC CGC CCG GCA CCC AGC GAC AAC CTG CCC CTG GTG GAC
 L   H   I   R   P   A   P   S   D   N   L   P   L   V   D>

140             150             160             170             180
      *               *               *               *               *
CTC ATC GAA CAC CCA GAC CCT ATC TTT GAC CCC AAG GAA AAG GAT
 L   I   E   H   P   D   P   I   F   D   P   K   E   K   D>

190             200             210             220
          *               *               *               *
CTG AAC GAG ACG CTG CTG CGC TCG CTG CTC GGG GGC CAC TAC GAC
 L   N   E   T   L   L   R   S   L   L   G   G   H   Y   D>

230             240             250             260             270
      *               *               *               *               *
CCA GGC TTC ATG GCC ACC TCG CCC CCC GAG GAC CGG CCC GGC GGG
 P   G   F   M   A   T   S   P   P   E   D   R   P   G   G>

280             290             300             310
          *               *               *               *
GGC GGG GGT GCA GCT GGG GGC GCG GAG GAC CTG GCG GAG CTG GAC
 G   G   G   A   A   G   G   A   E   D   L   A   E   L   D>

320             330             340             350             360
      *               *               *               *               *
CAG CTG CTG CGG CAG CGG CCG TCG GGG GCC ATG CCG AGC GAG ATC
 Q   L   L   R   Q   R   P   S   G   A   M   P   S   E   I>

370             380             390             400
          *               *               *               *
AAA GGG CTA GAG TTC TCC GAG GGC TTG GCC CAG GGC AAG AAG CAG
 K   G   L   E   F   S   E   G   L   A   Q   G   K   K   Q>

410             420             430             440             450
      *               *               *               *               *
CGC CTA AGC AAG AAG CTG CGG AGG AAG TTA CAG ATG TGG CTG TGG
 R   L   S   K   K   L   R   R   K   L   Q   M   W   L   W>

460             470             480             490
          *               *               *               *
TCG CAG ACA TTC TGC CCC GTG CTG TAC GCG TGG AAC GAC CTG GGC
 S   Q   T   F   C   P   V   L   Y   A   W   N   D   L   G>

500             510             520             530             540
      *               *               *               *               *
AGC CGC TTT TGG CCG CGC TAC GTG AAG GTG GGC AGC TGC TTC AGT
 S   R   F   W   P   R   Y   V   K   V   G   S   C   F   S>
```

Fig. 1B

```
       550              560              570              580
        *                *                *                *
AAG CGC TCG TGC TCC GTG CCC GAG GGC ATG GTG TGC AAG CCG TCC
 K   R   S   C   S   V   P   E   G   M   V   C   K   P   S>

590              600              610              620              630
        *                *                *                *                *
AAG TCC GTG CAC CTC ACG GTG CTG CGG TGG CGC TGT CAG CGG CGC
 K   S   V   H   L   T   V   L   R   W   R   C   Q   R   R>

640              650              660              670
        *                *                *                *
GGG GGC CAG CGC TGC GGC TGG ATT CCC ATC CAG TAC CCC ATC ATT
 G   G   Q   R   C   G   W   I   P   I   Q   Y   P   I   I>

680              690
        *                *
TCC GAG TGC AAG TGC TCG TGC TAG
 S   E   C   K   C   S   C   *>
```

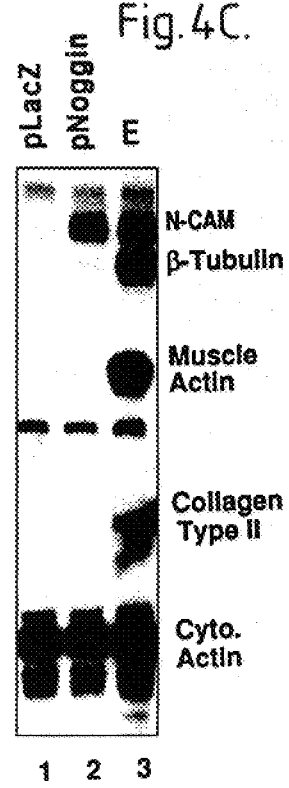

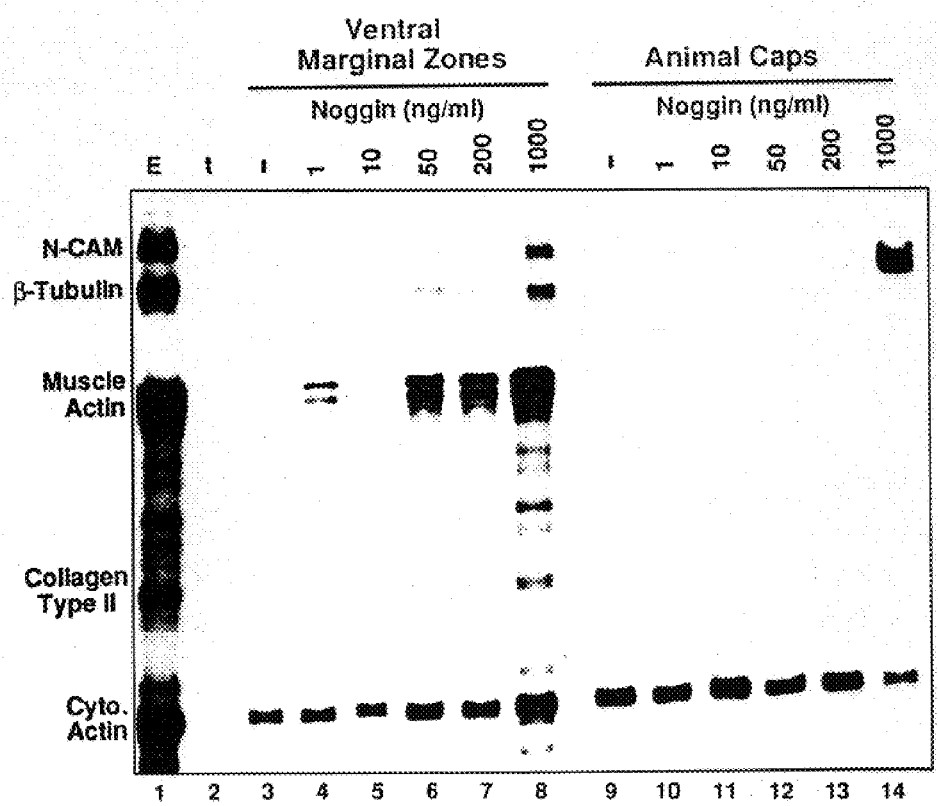

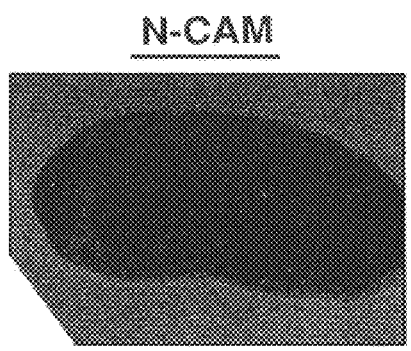
Fig. 7A. N-CAM
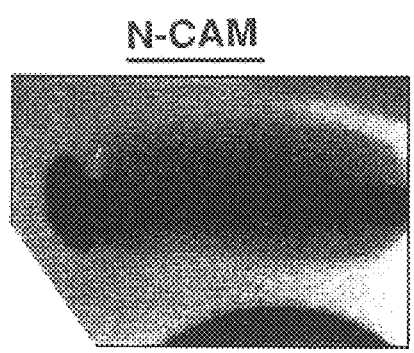
Fig. 7B. N-CAM
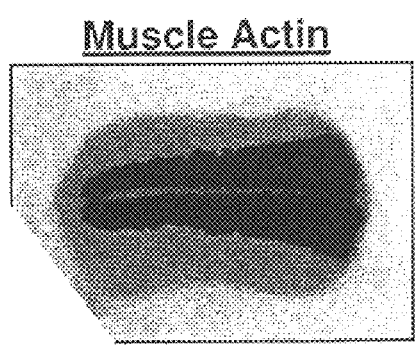
Fig. 7C. Muscle Actin

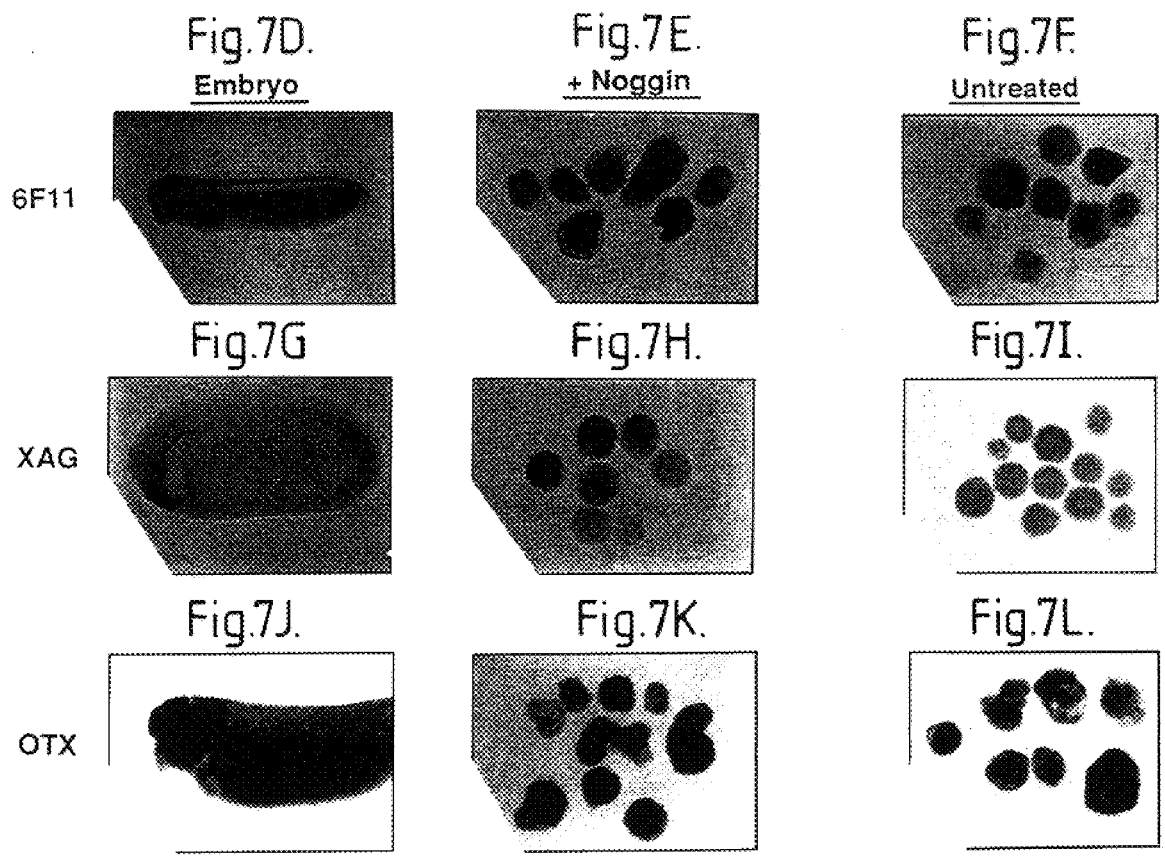

Fig.10
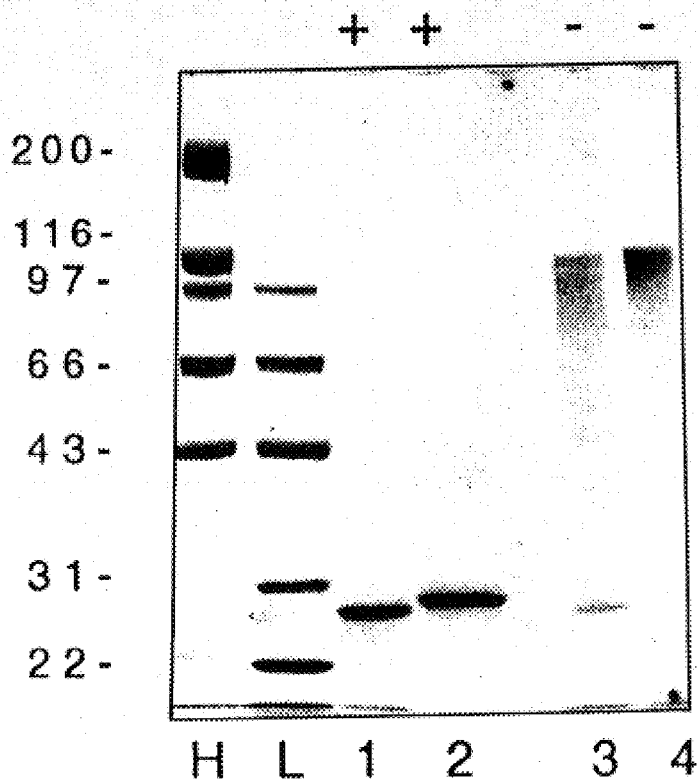
Fig.12.
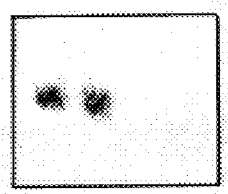
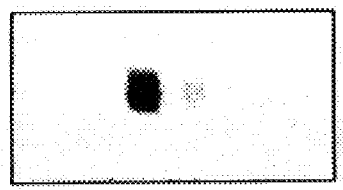
muscle actin

Fig. 13A

```
         5    10       15    20       25   30       35    40       45    50       55    60
         *             *             *             *             *             *
TAACTCACTC   ATTAGNCACC   CCAGCCTTAC   ACTTTATGCT   TCCGGCTCGT   ATGTTGTGTG 65    70       75    80       85    90       95   100      105   110      115   120
         *             *             *             *             *             *
GAATTGTGAG   CGGATAACAA   TTTCACACAG   GAAACAGCTA   TGACCATGAT   TACGCCAAGC 125   130      135   140      145   150      155   160      165   170      175   180
         *             *             *             *             *             *
TCGAAATTAA   CCCTCACTAA   AGGGAACAAA   AGCTGGAGCT   CCACCGCGGT   GGCGGCCGCC 185   190      195   200      205   210      215   220      225   230      235   240
         *             *             *             *             *             *
TTCCCAAGTA   GAGCGGCGGG   GGGGAATTGC   GACCAACTCG   TGCGCGTCTT   CTGCNCCGCG 245   250      255   260      265   270      275   280      285   290      295   300
         *             *             *             *             *             *
GCGGGAGCCG   GCGCTGCGCG   AACGGCTCTC   CTCGCAGCTC   ATGCTGCCTG   CCCTGCGCCT 305   310      315   320      325   330      335   340      345   350      355   360
         *             *             *             *             *             *
GCTCAGCCTC   GGGTGAGCCA   CCTCCGGAGG   GACCGGGGAG   CGCGGCAGCG   CCGCGGACTC 365   370      375   380      385   390      395   400      405   410      415   420
         *             *             *             *             *             *
GGCGTGCTCT   CCTCCGGGGA   CGCGGGACGA   AGAGGCAGCC   CCGGGGCGCG   CGCGGGAGGC 425   430      435   440      445   450      455   460      465   470      475   480
         *             *             *             *             *             *
ATGGAGCGCT   GCCCCAGCCT   GGGGGTCACC   CTCTACGCCC   TGGTGGTGGT   CCTGGGGCTG
 M  E  R     C  P  S  L   G  V  T     L  Y  A      L  V  V  V    L  G  L>

485   490      495   500      505   510      515   520      525   530      535   540
         *             *             *             *             *             *
CGGGCAGCAC   CAGCCGGCGG   CCAGCACTAT   CTACACATCC   GCCCAGCACC   CAGCGACAAC
 R  A  A     P  A  G  G   Q  H  Y      L  H  I     R  P  A  P    S  D  N>

545   550      555   560      565   570      575   580      585   590      595   600
         *             *             *             *             *             *
CTGCCCTTGG   TGGACCTCAT   CGAACATCCA   GACCCTATCT   TTGACCCTAA   GGAGAAGGAT
 L  P  L     V  D  L  I   E  H  P      D  P  I     F  D  P  K    E  K  D>

605   610      615   620      625   630      635   640      645   650      655   660
         *             *             *             *             *             *
CTGAACGAGA   CGCTGCTGCG   CTCGCTGCTC   GGGGGCCACT   ACGACCCGGG   CTTTATGGCC
 L  N  E     T  L  L  R   S  L  L      G  G  H     Y  D  P  G    F  M  A>

665   670      675   680      685   690      695   700      705   710      715   720
         *             *             *             *             *             *
ACTTCGCCCC   CAGAGGACCG   ACCCGGAGGG   GGCGGGGGAC   CGGCTGGAGG   TGCCGAGGAC
 T  S  P     P  E  D  R   P  G  G      G  G  G     P  A  G  G    A  E  D>

725   730      735   740      745   750      755   760      765   770      775   780
         *             *             *             *             *             *
CTGGCGGAGC   TGGACCAGCT   GCTGCGGCAG   CGGCCGTCGG   GGGCCATGCC   GAGCGAGATC
 L  A  E     L  D  Q  L   L  R  Q      R  P  S     G  A  M  P    S  E  I>

```
AAAGGGCTGG AGTTCTCCGA GGGCTTGGCC CAAGGCAAGA AACAGCGCCT GAGCAAGAAG
 K  G  L    E  F  S  E  G  L  A    Q  G  K    K  Q  R  L  S  K  K>

845  850   855  860   865  870   875  880   885  890   895  900
        *          *          *          *          *          *
CTGAGGAGGA AGTTACAGAT GTGGCTGTGG TCACAGACCT TCTGCCCGGT GCTGTACGCG
 L  R  R    K  L  Q  M  W  L  W   S  Q  T    F  C  P  V  L  Y  A>

905  910   915  920   925  930   935  940   945  950   955  960
        *          *          *          *          *          *
TGGAATGACC TAGGCAGCCG CTTTTGGCCA CGCTACGTGA AGGTGGGCAG CTGCTTCAGC
 W  N  D    L  G  S  R  F  W  P    R  Y  V    K  V  G  S  C  F  S>

965  970   975  980   985  990   995 1000  1005 1010  1015 1020
        *          *          *          *          *          *
AAGCGCTCCT GCTCTGTGCC CGAGGGCATG GTGTGTAAGC CATCCAAGTC TGTGCACCTC
 K  R  S    C  S  V  P  E  G  M    V  C  K    P  S  K  S  V  H  L>

1025 1030  1035 1040  1045 1050  1055 1060  1065 1070  1075 1080
        *          *          *          *          *          *
ACGGTGCTGC GGTGGCGCTG TCAGCGGCGC GGGGGTCAGC GCTGCGGCTG GATTCCCATC
 T  V  L    R  W  R  C  Q  R  R    G  G  Q    R  C  G  W  I  P  I>

1085 1090  1095 1100  1105 1110  1115 1120  1125 1130  1135 1140
        *          *          *          *          *          *
CAGTACCCCA TCATTTCCGA GTGTAAGTGT TCCTGCTAGA ACTCGGGGGG GGCCCCTGCC
 Q  Y  P   I  I  S  E   C  K  C    S  C  *>

1145 1150  1155 1160  1165 1170  1175 1180
        *          *          *          *
CGCGCCCAGA CACTTGATGG ATCCCCCGGG CTGAGATTTT
```

Fig. 14

```
          10         20         30         40         50         60         70         80
 †         *          *          *          *          *          * ¥        *          *
MERCPSLGVTLYALVVVLGL RATPAGGQHYLHIRPAPSDN LPLVDLIEHPDPIFDPKEKD LNETLLRSLLGGHYDPGFMA 90        100        110        120        130        140        150        160
           *          *          *          *          *          * †        *          *
TSPPEDRPGGGGGAAGGAED LAELDQLLRQRPSGAMPSEI KGLEFSEGLAQGLQMWLWSQ TFCPVLYAWNDLGSRFWPRY
                                                         Δ

170        180        190        200        210        220        230        240
 †        * †        †          *      †    *      †     *        † † *       ◊ *◊       *
VKVGSCFSKRSCSVPEGMVC KPSKSVHLTVLRWRCQRRGG QRCGWIPIQYPIISECKCSC SGDKTHTCPPCPAPELLGGP 250        260        270        280        290        300        310        320
           *          *    †     *          *          *          *¥*        *          *
SVFLFPPKPKDTLMISRTPE VTCVVVDVSHEDPEVKFNWY VDGVEVHNAKTKPREEQYNS TYRVVSVLTVLHQDWLNGKE 330        340        350        360        370        380        390        400
 †         *          *          *          *         †*          *          *          *
YKCKVSNKALPAPIEKTISK AKGQPREPQVYTLPPSREEM TKNQVSLTCLVKGFYPSDIA VEWESNGQPENNYKTTPPVL 410        420        430        440        450
           *          *        † *          *          *
DSDGSFFLYSKLTVDKSRWQ QGNVFSCSVMHEALHNHYTQ KSLSLSPGK·
```

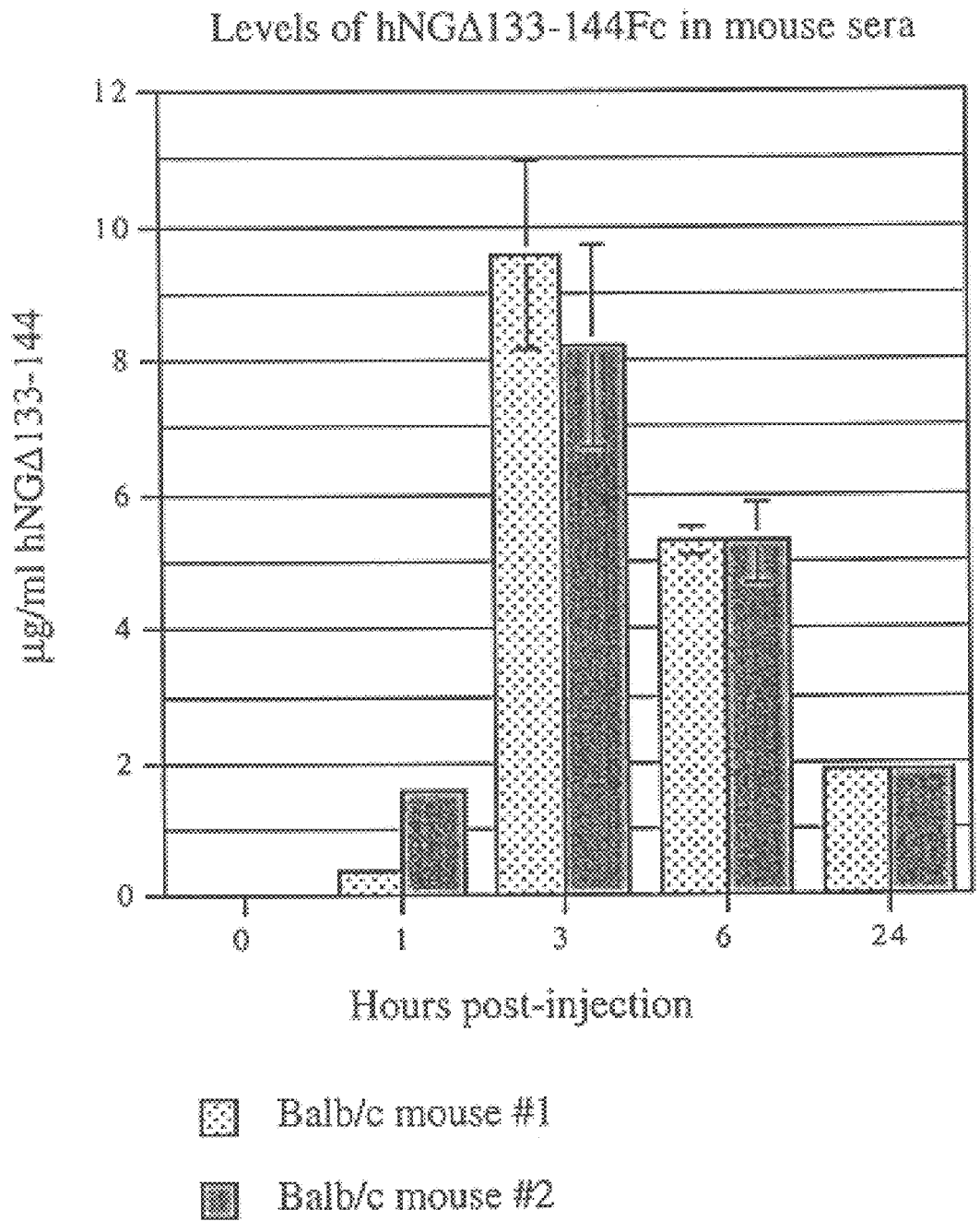

6,075,007

MODIFIED NOGGIN POLYPEPTIDE AND COMPOSITIONS

This invention generally relates to a growth factor with dorsal growth inducing activity, and more particularly to a modified form of the Spemann organizer signal Noggin, to compositions comprising the modified Noggin, and to DNA or RNA sequences comprising coding (sense) or antisense sequences for the modified Noggin.

Throughout this application, various publications are referenced. The disclosures of those publications, in their entireties, are hereby incorporated by reference into the subject application.

BACKGROUND OF THE INVENTION

Growth factors are substances, such as polypeptide hormones, which affect the growth of defined populations of animal cells in vivo or in vitro, but which are not nutrient substances. Proteins involved in the growth or differentiation of tissues may promote or inhibit growth or differentiation, and thus the general term "growth factor" includes cytokines and trophic factors.

Growth factors, their receptors, DNA or RNA coding or antisense sequences therefore, and fragments thereof, are useful in a number of therapeutic, clinical, research, diagnostic, and drug design applications. See, for example, U.S. Pat. No. 4,857,637, issued Aug. 15, 1989 (method for immunizing an animal against its growth hormone receptor); U.S. Pat. No. 4,933,294, issued Jun. 12, 1990 (assays and therapies involving the human EGF receptor); U.S. Pat. No. 5,030,576, issued Jul. 9, 1991 (the role of receptors and receptor hybrids in drug design and drug screening by the pharmaceutical industry); U.S. Pat. No. 5,087,616, issued Feb. 11,1992 (method for destroying tumor cells using a composition comprising a growth factor conjugate); U.S. Pat. No. 5,098,833, issued Mar. 24, 1992 (expression systems useful in therapeutic or diagnostic compositions); and International Application Publication No. WO92/05254, published Apr. 2, 1992 (various aspects of isolation, preparation, and applications for a novel neurotrophic factor); each of which is incorporated herein by reference.

The Spemann organizer induces neural tissue from dorsal ectoderm and dorsalizes lateral and ventral mesoderm in Xenopus. The first molecule to have the properties expected of a Spemann organizer signal was identified in an expression screen for activities that induce dorsal structures in Xenopus embryos and was called Noggin (Smith, W. C. and Harland, R. M. Cell 70: 829–840 (1992)). Organizer signals such as Noggin may be antagonized by members of the bone morphogenetic protein (BMP) class of the transforming growth factor beta (TGF-β) gene superfamily. It was recently reported that Noggin protein binds BMP-4 with high affinity and can abolish BMP-4 activity by blocking binding to cognate cell surface receptors (Zimmerman, L. B., et al., Cell 86: 599–606 (1996)).

In addition to their roles in normal bone formation, the BMPs appear to be involved in diseases in which they promote abnormal bone growth. For example, BMPs have been reported to play a causative role in the disease known as Fibrodysplasia Ossificans Progressiva (FOP), in which patients grow an abnormal "second skeleton" that prevents any movement.

DESCRIPTION OF THE DRAWINGS

FIGS. 1A and 1B—Nucleotide sequence (SEQ ID NO:1) for the human noggin gene and deduced amino acid sequence (SEQ ID NO: 2). The KKLRRK deletion that is described in Example 9 (hNGΔ138–144) as adequate for reducing the interaction with heparin to that expected for ionic effects is encoded beginning at nucleotide 415 (AAG . . . ).

FIG. 4A—Time course of animal caps treated with purified noggin vs. activin; direct vs indirect neural induction. Animal caps were dissected as shown in FIG. 2A and treated with LCMR+0.5% BSA (U), a 20% dilution of activin conditioned COS cell medium (A), or 1 μg/ml purified human noggin (N). RNA isolated from treated animal caps (lanes 2–13) along with St22 whole embryo RNA (lane1) and tRNA (lane 14) was probed for N-CAM, β-tubulin, muscle and cytoskeletal actins, collagen type II, and EF-1a.

FIG. 4B—Expression of early mesoderm markers in activin but not noggin induced animal caps. Animal caps were dissected from St8 embryos, treated as described in (FIG. 4A), and harvested at St11. Lanes 1 and 2 respectively show goosecoid and Xbra probe protection by St10.5 whole embryo RNA. Lanes 3–6 show protection by a mix of these two probes. Relative RNA levels are demonstrated by separate EF-1α probe protection.

FIG. 4C—Plasmid directed gastrula stage noggin expression directly induces neural tissue. One cell stage embryos were injected with 20 pg of pCSKAlacZ or pCSKAnoggin into the animal pole. Animal caps from injected embryos were dissected at St8–9 and cultured until St20, when they were harvested for analysis by RNase protection.

FIG. 6—Dose response of ventral marginal zones and animal caps to human noggin protein. St 10.5 VMZs and St9 animal caps were dissected as shown in FIG. 2A, and treated with 0, 1, 10, 50, 200, and 1000 ug/ml of human noggin (lanes 3–8 and 10–15 respectively). RNA from treated explants and control whole embryos aged to St26 was then analyzed by RNase protection, using the probes N-CAM, β-tubulin, actin and collagen type II. In this experiment, muscle induction at the dose of 1 ng/ml is stronger than at 10 ng/ml, and there is a low level of muscle actin expression in the uninduced VMZs. This could be due to experimental variability since in repeated experiments we saw muscle induction only at the doses of 50 ng/ml and above.

FIGS. 7A to 7L—In situ hybridization and antibody staining. Tailbud embryos stained for NCAM showing side and dorsal views (7A, 7B); NCAM RNA is only detected in the neural tube, and not the somites. For comparison, somites of a tailbud embryo stain for muscle actin, dorsal view (7C). Neural specific 6F11 antibody staining at St30 (7D–7F). Some cement gland pigment remained in these embryos after bleaching as seen in (7D), however this pigment is distinct from antibody staining. The inner mass of staining in the noggin treated animal caps is due to the 6F11 antibody detection. Cement gland specific XAG-1 transcripts detected at St23 (7G–7i), and anterior brain otxA trasncripts detected at St35 (7J–7L) in whole embryos at (7D,7G,7J), human noggin treated (1 μg/ml) animal caps (7E,7H,7K), and untreated animal caps (7F,7i,7L).

FIG. 10—Recombinant noggin produced in E. coli and in insect cells analyzed by 12.5% SDS-PAGE. Lanes H, L: High and low molecular weight markers of the indicated size, respectively. Lanes 1,2: Recombinant noggin produced in E. Coli and in insect cells respectvely, treated with 2-mercaptoethanol before electrophoresis. The slower mobility of noggin from insect cells correponds to the size increase that would occur due to N-linked glycosylation at the single consensus site. Lanes 2,3: Recombinant noggin produced in E. coli and in insect cells respectvely, not treated with 2-mercaptoethanol before electrophoresis.

FIG. 12—Ventral marginal zone assay showing induction of muscle actin mRNA after exposure to human noggin (0.01, 0.05, 0.2 μg/ml) produced in baculovirus, a mock transfected culture of baculovirus (0.02, 1 μg/ml) or human noggin produced in E.coli (0.1, 0.5, 2, or 10 μg/ml).

FIGS. 13A and 13B—Nucleotide sequence (SEQ ID NO:10) for the mouse noggin gene and deduced amino acid sequence (SEQ ID NO:11).

FIG. 14—Amino acid sequence of hNGΔ133–144Fc (SEQ ID NO:23)
The putative signal peptide sequence of human noggin (hNG) is shown in italics.
(†) marks the position of cysteines (C), except as noted below.
(¥) marks the position of N-linked glycosylation sites.
(Δ) marks the position in which the Δ133–144 deletion was created.
The sequence of amino acids 133 to 144 in the wild-type hNG is KKQRLSKKLRRK and may be referred to as the 'basic region' of hNG. The CYS involved in inter-chain disulfide bridges in hNG is marked in bold ( . . . SECKCSC . . . ).
The position of the Ser-Gly bridge that connects the hNGΔ133–144 sequence with the constant region of human IgG1 (Fc) is shown in bold (SG). The sequence of the Fc domain is shown underlined.
(◊) marks the two cysteines (amino acids number 371 and 374) of the IgG hinge preceding the Fc that form the inter-chain disulfide bridges that link two Fc domains of human IgG1.
(·) shows the position of the STOP codon.

Figure 16:
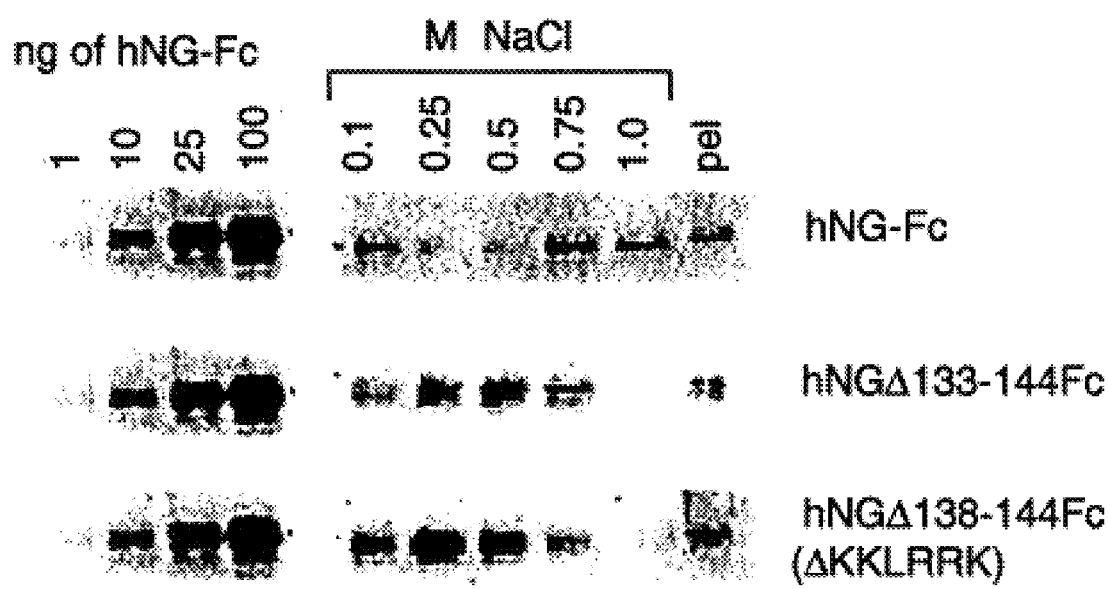
FIG. 16—hNGΔ133–144Fc binds to heparin with reduced affinity
Approximately 1 μg of hNG-Fc, hNGΔ138–144Fc, or hNGΔ133–144Fc each were incubated with 50 μl heparin·agarose (Pierce) in 1 ml 1% BSA in PBS. After 1 hour of incubation at room temperature the heparin·agarose beads were precipitated by centrifugation, resuspended in PBS and moved to new tubes. Subsequently each pellet was sequentially washed with 100 μl of 0.1, 0.25, 0.5, 0.75, and 1.0 M NaCl and the supernatant derived from each of these steps was kept for loading on a 4 to 12% NuPAGE/MES gels (Novex) under reducing conditions. ⅕ of each supernatant and the resuspended heparin·agarose pellet was loaded onto the gels. The Fc-tagged hNGs were visualized by western blotting using a Horse Radish Peroxidase conjugated anti-human IgG antibody (Rockland, Inc.) followed by chemiluminescent detection (Pierce).

hBMP4 (2 µg/ml) was coated on ELISA plates (Immulon4 from Dynatech) by passive binding. Unbound hBMP4 was removed by washing four times with PBS, and the plates were blocked with 1% BSA in PBS. A standard curve of hNGΔ133–144Fc was performed. After a 1 hour incubation unbound hNG-Fc or hNGΔ133–144Fc was removed by washing four times with PBS, and 0.5 µg/ml anti-human IgG·Alkaline Phosphatase conjugate (anti-Fc·AP) was added to the plate and processed as described above (FIG. 16). The level of hNGΔ133–144Fc in the sera collected at each time point was determined by performing serial dilutions of each serum sample on the hBMP4-coated ELISA plates, and detecting Fc-immunoreactivity using the assay described above. A405 units were then converted to concentrations of hNGΔ133–144Fc and plotted as a function of time.

Note: The amount of serum proteins present in these assays did not interfere with the binding and detection of hNGΔ133–144Fc.

Figure 17B:
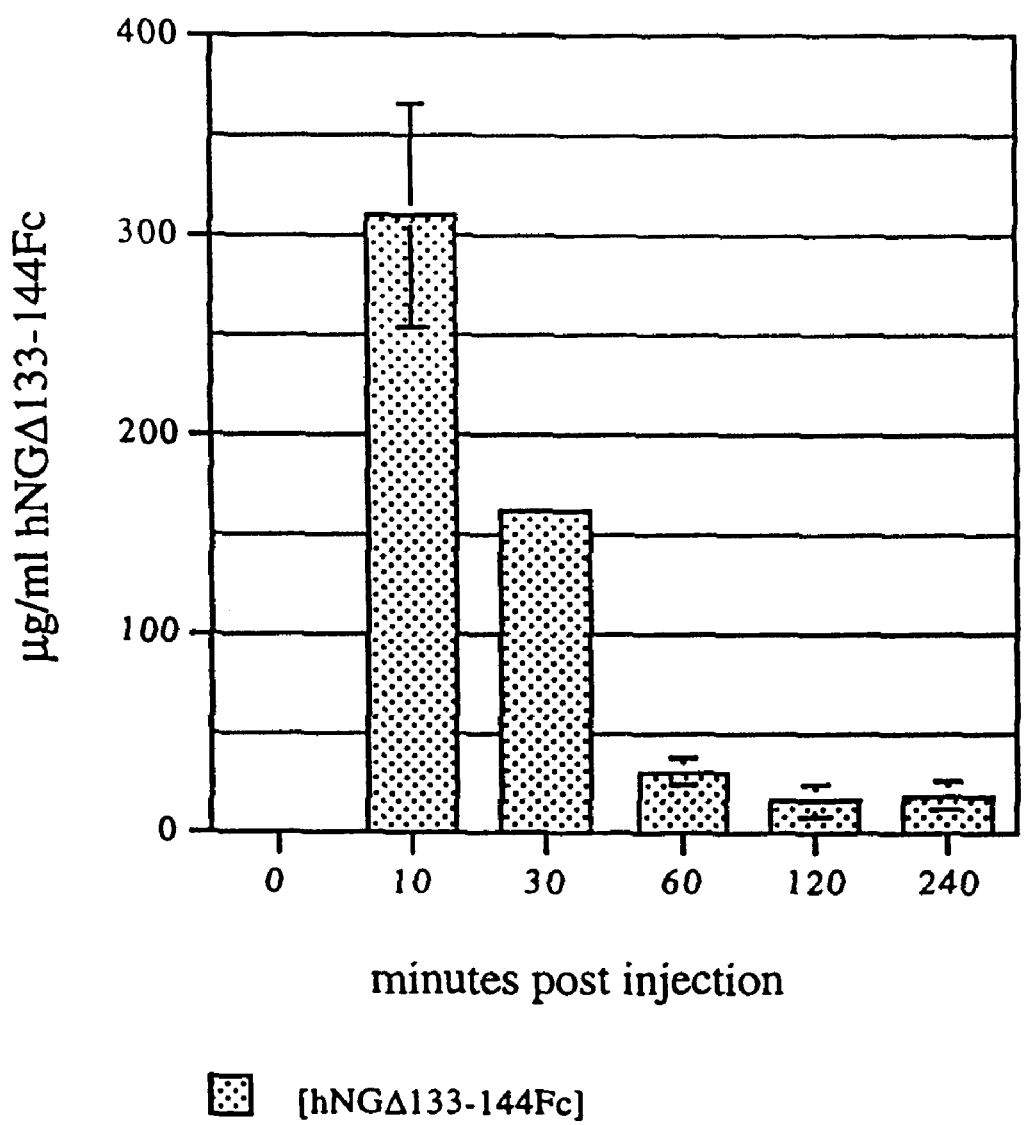
FIG. 17A—hNGΔ133–144Fc pharmacokinetics in mice
0.1 mg of hNGΔ133–144Fc were injected into six week old Balb/c male mice (2 mice, 0.1 mg/mouse) intraperitoneously (ip). Prior to injection a sample of blood was collected from each mouse ('pre-bleed'). Subsequently, blood was drawn from the mice at 1, 3, 6 and 24 hours post-injection. Serum was prepared from these samples by following standard serological procedures, and the levels of biologically active hNGΔ133–144Fc available in the sera of Bab/c mice after the ip-injection were determined by using a functional ELISA.

FIG. 17B—hNGΔ133–144Fc pharmacokinetics in rats 1.0 mg of hNGΔ133–144Fc was injected into a 250 gram adult male rat intravenously (iv). Prior to injection, a sample of blood was collected ('pre-bleed'). Subsequently, blood was drawn from the rat at 10, 30, 60, 120, and 240 minutes post-injection. Serum was prepared from these samples by following standard serological procedures and the levels of biologically active hNGΔ133–144Fc available in the serum samples were determined by using the functional ELISA described in FIG. 17A.

SUMMARY OF THE INVENTION

Polypeptides of the invention induce dorsal growth in vertebrates and can be prepared in soluble, physiologically active form for a number of therapeutic, clinical and diagnostic applications.

In a preferred embodiment, human noggin protein as set forth in FIGS. 1A–1B (SEQ ID NO: 2) or modified noggin protein (SEQ ID NO:23) as set forth, for example, in FIG. 14, is prepared for use in therapeutic, clinical and diagnostic applications.

In another aspect of the present invention an oligonucleotide, such as cDNA, is provided having substantial similarity to (or being the same as) Xenopus noggin partial mouse noggin SEQ ID NO: 1 or SEQ ID NO:10. This oligonucleotide can be single or double stranded, be formed of DNA or RNA bases, and can be in the antisense direction with respect to Xenopus noggin, partial mouse noggin, SEQ ID NO: 1 or SEQ ID NO: 10. Xenopus noggin, partial mouse noggin, SEQ ID NO:1 each code and SEQ ID NO:10 for a functional polypeptide that we have designated "noggin," which is capable of inducing dorsal development in vertebrates when expressed.

Noggin or fragments or muteins thereof (which also may be synthesized by in vitro methods) may be fused (by recombinant expression or in vitro covalent methods) to an immunogenic polypeptide and this, in turn, may be used to immunize an animal in order to raise antibodies against a noggin epitope. Anti-noggin is recoverable from the serum of immunized animals. Alternatively, monoclonal antibodies may be prepared from cells to the immunized animal in conventional fashion. Antibodies identified by routine screening will bind to noggin but will not substantially cross-react with "wnt" or other growth factors. Immobilized anti-noggin antibodies are useful particularly in the diagnosis (in vitro or in vivo) or purification of noggin.

Substitutional, deletional, or insertional mutants of noggin may be prepared by in vitro or recombinant methods and screened for immuno-crossreactivity with noggin and for noggin antagonist or agonist activity.

Noggin or fragments or muteins thereof also may be derivatized in vitro in order to prepare immobilized noggin and labelled noggin, particularly for purposes of diagnosis of noggin or its antibodies, or for affinity purification of noggin antibodies.

The present invention further provides for expression of biologically active noggin molecules in prokaryotic and eukaryotic expression systems.

The present invention further provides for the production of noggin or fragments or muteins thereof in quantities sufficient for therapeutic and diagnostic applications. Likewise, anti-noggin antibodies may be utilized in therapeutic and diagnostic applications. For most purposes, it is preferable to use noggin genes or gene products from the same species for therapeutic or diagnostic purposes, although cross-species utility of noggin may be useful in specific embodiments of the invention.

In additional embodiments, the noggin nucleic acids, proteins, and peptides of the invention may be used to induce neural tissue formation or block BMP activity in mammals.

DETAILED DESCRIPTION OF THE INVENTION

Throughout this application, when nucleic acid sequences that encode polypeptides are set forth, it is understood that the complementary strand of the coding sequence is thereby taught as well.

We have discovered a structurally unique growth factor that is readily available in substantially pure, soluble form. We have named the inventive polypeptide "noggin." This growth factor induces dorsal development and blocks BMP activity in vertebrates.

An earlier described family of proteins that also induces dorsal development are the "wnt" proteins. These, however, in contrast to noggin remain tenaciously bound to cell surfaces. Our initial work with noggin has been in Xenopus embryos; however, noggin is highly conserved among vertebrates, as our work with mouse noggin has demonstrated. The prior known FGF growth factor family is also known to be involved in early embryonic induction, but both the FGF proteins and their receptors are distinctly different from noggin. Noggin modifies the actions of FGF (and also activin), for example by potentiating growth, and is thus particularly suggested in therapeutic compositions for use in combination with other growth factors (as therapeutic adjuvants), such as to modify or potentiate their effects.

We have cloned cDNA for noggin. The noggin cDNA contains a single reading frame encoding a 26 kDa protein with a hydrophobic amino-terminal sequence. Noggin is secreted. Noggin's cDNA encodes the protein as a 26 kDa protein, but we have determined that noggin is secreted in vivo, apparently as a dimeric glycoprotein with a starting apparent molecular weight of about 33 kDa (as the wild-type subunit). When not glycosylated, the monomeric unit has an apparent molecular weight on SDS PAGE of about 25–30 kDa.

We have cloned the gene for human noggin (FIGS. 1A–1B; SEQ ID NO: 1). The sequence codes for a protein which has noggin activity (SEQ ID NO: 2). The carboxy terminal region of noggin shows homology to a Kunitz-type protease inhibitor, indicating that noggin protein, or fragments thereof, may exhibit activities of a protease inhibitor.

We have been able to express biologically active noggin in both eukaryotic and prokaryotic host cells. Two expression systems we have successfully used to express biologically active noggin have been mammalian cell lines (COS and mouse 293). A third expression system is injection of synthetic mRNA into Xenopus oocytes. In addition, we have successfully expressed biologically active human noggin in a prokaryotic system, E. coli, and in baculovirus.

Expression in these several different systems also illustrates the high degree of conservation for noggin. We have found, for example, substantial sequence similarity between frog noggin and mouse noggin with a number of completely conserved stretches. Thus, the following amino acid sequences represent completely conserved portions as between frog noggin and mouse noggin:

QMWLWSQTFCPVLY (SEQ ID NO:3);

RFWPRYVKVGSC (SEQ ID NO:4);

SKRSCSVPEGMVCK (SEQ ID NO:5);

LRWRCQRR (SEQ ID NO:6); and,

ISECKCSC (SEQ ID NO:7).

There is about 87% overall conservation between the mouse and frog sequences, and we have also observed a unique cysteine distribution between the two.

Noggin nucleic acids, or oligonucleotides, encode a noggin polypeptide or hybridize to such DNA and remain stably bound to it under stringent conditions and are greater than about 10 bases in length; provided, however, that such hybridizing nucleic acid is novel and unobvious over any prior art nucleic acid including that which encodes or is complementary to nucleic acid encoding other growth factors.

By "stringent conditions" is meant those which (1) employ low ionic strength and high temperature for washing, for example, 0.15 M NaCl/0.015 M sodium citrate/ 0.1% NaDodSo$_4$ at 50° C., or (2) use during hybridization a denaturing agent such as formamide, for example, 50% (vol/vol) formamide with 0.1% bovine serum albumin/ 0.1%Ficoll/0.1% polyvinylpyrrolidone/50 mM sodium phosphate buffer at pH 6.5 with 750 mM NaCl, 75 mM sodium citrate at 42° C.

By "substantial similarity," when we are referring to a nucleotide sequence, is meant cross hybridization of sequences under conditions of moderate stringency using a probe greater than 100 nucleotides long at 30° C. in a standard buffer (Wahl et al., PNAS 76: 3683) and washes at 37° C. in 300 mM NaCl, 30 mM sodium citrate, 0.2% SDS at pH 7. Alternatively, one is able to isolate, by polymerase chain reaction, a fragment of DNA coding for noggin or noggin family members when using primers of degenerate sequence that encode those SEQ ID NOS:3–7.

By "substantial similarity" when reference is made to proteins is that noggin from different species, or noggin family members within a species, will preserve the positions of cysteine residues in at least 80% of positions throughout the protein. Like the neurotrophin family, the sequence of the mature form of noggin and noggin related polypeptides will be identical in at least 40% of positions. Substantial similarity at the protein level includes an ability of a subject protein to compete with noggin for binding to receptors and some (but not all) monoclonal antibodies raised against noggin epitopes.

The cloned cDNA for noggin (derived from frog) is designated herein as Xenopus noggin, partial sequence from mouse is designated herein as partial mouse noggin, the full sequence of mouse noggin as shown in FIGS. 13A–13B is designated herein as (SEQ ID NO: 10). The human sequence is designated herein as SEQ ID NO: 1. We have used RNA transcripts from the Xenopus noggin clone to rescue embryos and return them to substantially normal development when the noggin RNA is injected into ventralized embryos. In high doses this results in excessive head development and it is for this reason we named the protein "noggin." In Northern blot analysis, the noggin cDNA hybridizes to two mRNAs that are expressed both maternally and zygotically.

When using nucleotide sequences coding for part or all of noggin in accordance with this invention, the length of the sequence should be at least sufficient in size to be capable of hybridizing with endogenous mRNA for the vertebrate's own noggin. Typically, sufficient sequence size (for example, for use as diagnostic probes) will be about 15 consecutive bases (DNA or RNA). In some diagnostic and therapeutic applications, one may wish to use nucleotide noggin coding sequences (analogous to all or a portion of Xenopus noggin, partial mouse noggin, SEQ ID NO: 10 SEQ ID NO:1 or SEQ ID NO:23 in the anti-sense direction with respect to either Xenopus noggin, partial mouse noggin, SEQ ID NOS: 10, 1, or 23.

We suggest as a few preferred primers for amplifying noggin from other species (e.g. human):

5' Primer 1 SEQ ID NO: 12

C A A/G A C N T T C/T T G C/T C C N G T N

5' Primer 2 SEQ ID NO: 13

T T C/T T G G C C N C/A G N T A C/T G T N A A A/G G T N G G

5' Primer 3 SEQ ID NO: 14

C C N G A A/G G G N A T G G T N T G

3' Primer 1 SEQ ID NO: 15

C A N C/G T/A A/G C A C/T T T A/G C A C/T T C

3' Primer 2 SEQ ID NO: 16

C A N A C C A T N C C C/T T C N G G

3' Primer 3 SEQ ID NO: 17

C G/T N C G/T T/C T G G/A C A N C G/T C C A where N represents a mixture of all four nucleotides and mixtures of two nucleotides are represented by alternates (e.g. A/G).

Although noggin transcript is not localized in the oocyte and cleavage stage embryo, zygotic transcripts are initially restricted to the presumptive dorsal esoderm, and reach their highest levels at the gastrula stage in the dorsal lip of the blastopore (Spemann's organizer). In the neurula, noggin is transcribed in the notochord and prechordal mesoderm.

Without being bound by theory, we have formulated hypotheses about the embryological effects of noggin based on where it is expressed, and on the effects of RNA injection in embryos. Since noggin is expressed in the Spemann organizer, we believe noggin to be a mediator of the effects of the Spemann organizer, namely neural induction and dorsalization of the mesoderm. We have shown that noggin is able to directly induce neural tissue formation. Since noggin is expressed in the notochord and head mesoderm, we believe noggin to influence either the dorsal-ventral pattern or anterior-posterior pattern of the neural plate. Since noggin is expressed in the branchial arch neural crest, we believe it may therefore influence whether neural crest cells deposit cartilage and also to influence later branchial arch growth and remodelling. Noggin is expressed in the tail fin neural crest, and since neural crest is required for growth of the fin, noggin may act as a growth factor for epidermis or mesenchyme.

Although much of our experimental work has involved rescue of embryonic development, because expression in the notochord persists in the growing tail bud and a discontinuous line of stained cells (indicating expression of noggin initiated at new sites) runs the length of the roof plate of the neural tube (and is also apparent in the head mesoderm), we believe noggin is expressed as an adult cell function also.

A number of applications for noggin are suggested from its properties. The noggin cDNA should be useful as a diagnostic tool (such as use of oligonucleotides as primers in a PCR test to amplify those with sequence similarities to the oligonucleotide primer, and to see how much noggin is present, e.g. primers such as 5' Primers 1–3 and 3' Primers 1–3).

Because noggin has a pattern of expression that suggests it is used to regulate cartilage production in the embryonic head, clinical uses to regulate cartilage and bone growth are suggested for noggin in therapeutic compositions and particularly in combination with other growth factors due to a property of noggin to potentiate at least some growth factors. Since neural crest cells are required for the tadpole fin to grow, noggin seems to be a growth factor for the tissue matrix and epidermis and should prove useful, for example, in wound healing compositions.

When one views noggin as ligand in complexes, then complexes in accordance with the invention include antibody bound to noggin, antibody bound to peptides derived from noggin, noggin bound to its receptor, or peptides derived from noggin bound to its receptor. Mutant forms of noggin, which are either more potent agonists or antagonists, or have improved propeerties such as increased bioavailability, are believed to be clinically useful. Such complexes of noggin and its binding protein partners will find uses in a number of applications.

Practice of this invention includes use of an oligonucleotide construct comprising a sequence coding for noggin and for a promoter sequence operatively linked to noggin in a mammalian, bacterial or a viral expression vector. Expression and cloning vectors contain a nucleotide sequence that enables the vector to replicate in one or more selected host cells. Generally, in cloning vectors this sequence is one that enables the vector to replicate independently of the host chromosomes, and includes origins of replication or autonomously replicating sequences. The well-known plasmid pBR322 is suitable for most gram negative bacteria, the $2\mu$ plasmid origin for yeast and various viral origins (SV40, polyoma, adenovirus, VSV or BPV) are useful for cloning vectors in mammalian cells.

Expression and cloning vectors should contain a selection gene, also termed a selectable marker. Typically, this is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies.

Examples of suitable selectable markers for mammalian cells are dihydrofolate reductase (DHFR) or thymidine kinase. Such markers enable the identification of cells which were competent to take up the noggin nucleic acid. The mammalian cell transformants are placed under selection pressure in which only the transformants are uniquely adapted to survive by virtue of having taken up the marker.

Selection pressure is imposed by culturing the transformants under conditions in which the concentration of selection agent in the medium is successively changed. Amplification is the process by which genes in greater demand for the production of a protein critical for growth are reiterated in tandem within the chromosomes of successive generations of recombinant cells. Increased quantities of noggin can therefore be synthesized from the amplified DNA.

For example, cells transformed with the DHFR selection gene are first identified by culturing all of the transformants in a culture medium which contains methotrexate (Mtx), a competitive antagonist of DHFR.

An appropriate host cell in this case is the Chinese hamster ovary (CHO) cell line deficient in DHFR activity, prepared and propagated as described by Urlaub and Chasin, Proc. Nat. Acad. Sci., 77, 4216 (1980). The transformed cells then are exposed to increased levels of Mtx. This leads to the synthesis of multiple copies of the DHFR gene and, concomitantly, multiple copies of other DNA comprising the expression vectors, such as the DNA encoding noggin. Alternatively, host cells transformed by an expression vector comprising DNA sequences encoding noggin and aminoglycoside 3' phosphotransferase (APH) protein can be selected by cell growth in medium containing an aminoglycosidic antibiotic such as kanamycin or neomycin or G418. Because eukarotic cells do not normally express an endogenous APH activity, genes encoding APH protein, commonly referred to as neo resistant genes, may be used as dominant selectable markers in a wide range of eukaryotic host cells, by which cells transformed by the vector can readily be identified.

Expression vectors, unlike cloning vectors, should contain a promoter which is recognized by the host organism and is operably linked to the noggin nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters can be operably linked to noggin encoding DNA by removing them from their gene of origin via restriction enzyme digestion, followed by insertion 5' to the start codon for noggin.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exist, then synthetic oligonucleotide adapters or linkers are used in accord with conventional practice.

Transcription of noggin-encoding DNA in mammalian host cells is controlled by promoters obtained from the genomes of viruses such as polyoma, cytomegalovirus, adenovirus, retroviruses, hepatitis-B virus, and most preferably Simian Virus 40 (SV40), or from heterologous mammalian promoters, e.g. the actin promoter. Of course, promoters from the host cell or related species also are useful herein.

In particular embodiments of the invention expression of noggin in *E. coli* is preferably performed using vectors which comprise the following: a lac UV5 promoter which may be controlled by the lactose operon repressor; a strong ribosome binding site, for example, the ribosome binding site of bacteriophage T7; a mutation in the replication control region of the plasmid which may increase copy number; and a mutation which limits the expression of the antibiotic resistance protein.

In a preferred embodiment, noggin is expressed in a high copy number kanamycin resistant pBR322-derived plasmid under the control of a lac UV5 promoter. In an additional preferred embodiment, noggin is expressed in baculovirus under the control of the polyhedrin promoter of *Autographa californica* Multiple Nuclear Polyhedrosis virus in insect host cells.

An object of the present invention is to provide novel modified Noggin molecules for the treatment of diseases or disorders including, but not limited to, Fibrodysplasia Ossificans Progressiva (FOP), as well as for treating abnormal bone growth, such as the pathological growth of bone following hip replacement surgery, trauma, burns or spinal cord injury.

A further object of the present invention is to provide a method for producing modified Noggin molecules, other than those specifically described herein, that have improved therapeutic properties.

These and other objects are achieved in accordance with the invention, whereby amino acid deletions in human Noggin protein enhance its therapeutic properties.

Thus, according to the invention, certain amino acid deletions in the human Noggin protein result in a modified human Noggin protein that exhibits improved bioavailability in animal sera while retaining the ability to bind to a Bone Morphogenetic Protein. Such a modified Noggin protein would be expected to have enhanced therapeutic properties.

The present invention also provides for pharmaceutical compositions comprising a modified Noggin molecule, as described herein and a suitable pharmaceutical carrier.

The active ingredient, which may comprise the modified Noggin, should be formulated in a suitable pharmaceutical carrier for systemic or local administration in vivo by any appropriate route including, but not limited to injection (e.g., intravenous, intraperitoneal, intramuscular, subcutaneous, endoneural, perineural, intraspinal, intraventricular, intravitreal, intrathecal etc.), by absorption through epithelial or mucocutaneous linings (e.g., oral mucosa, rectal and intestinal mucosa, etc.); or by a sustained release implant, including a cellular or tissue implant.

Depending upon the mode of administration, the active ingredient may be formulated in a liquid carrier such as saline, incorporated into liposomes, microcapsules, polymer or wax-based and controlled release preparations, or formulated into tablet, pill or capsule forms.

The concentration of the active ingredient used in the formulation will depend upon the effective dose required and the mode of administration used. The dose used should be sufficient to achieve circulating plasma concentrations of active ingredient that are efficacious. Effective doses may be extrapolated from dose-response curves derived from in vitro or animal model test systems.

Practice of this invention includes preparation and uses of a diagnostic or therapeutic agent comprising a nucleotide sequence of at least about 15 DNA or RNA bases analogous to all or a portion of either SEQ ID. NO: 23, Xenopus noggin, partial mouse noggin, SEQ ID NO: 10; or SEQ ID NO: 1 or of the nucleic acid sequences contained in bacteriophages, hnogλ-9 or hnogλ-10. That is, noggin preparations are useful as standards in assays for noggin and in competitive-type receptor binding assays when labelled with radioiodine, enzymes, fluorophores, spin labels, and the like. Therapeutic formulations of noggin are prepared for storage by mixing noggin having the desired degree of purity with optional physiologically acceptable carriers, excipients or stabilizers, in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin or immunoglobulins. Other components can include glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

Noggin may be used according to the invention as described supra. The concentration of the active ingredient used in the formulation will depend upon the effective dose required and the mode of administration used. The dose used should be sufficient to achieve circulating plasma concentrations of active ingredient that are efficacious. Effective doses may be extrapolated from dose-response curves derived from in vitro or animal model test systems.

By referring to noggin, the present invention also contemplates the use of fragments, derivatives, muteins, agonists or antagonists of noggin molecules.

Noggin may be administered in any pharmaceutically acceptable carrier. The administration route may be any mode of administration known in the art, including but not limited to intravenously, intrathecally, subcutaneously, by injection into involved tissue, intraarterially, intranasally, orally, or via an implanted device. The present invention provides for pharmaceutical compositions comprising noggin in a pharmaceutically acceptable carrier.

Administration may result in the distribution of noggin throughout the body or in a localized area. For example, in some conditions which involve distant regions of the nervous system, intravenous or intrathecal administration of noggin may be desirable. Alternatively, and not by way of limitation, when localized regions of the nervous system are involved, local administration may be desirable. In such situations, an implant containing noggin may be placed in or near the lesioned area. Suitable implants include, but are not limited to, gelfoam, wax, or microparticle-based implants.

Inventive complexes comprise a ligand characterized by one or more of the SEQ ID NOS:3–7. The ligand can be bound to a protein, such as antibody. Such antibodies can be polyclonal or monoclonal. Polyclonal antibodies to noggin generally are raised in animals by multiple subcutaneous (sc) or intraperitoneal (ip) injections of noggin and an adjuvant. It may be useful to conjugate noggin or a fragment containing the target amino acid sequence to a protein which is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (coniugation through cysteine residues), N-hydroxy-succinimide (through lysine residues), glutaraldehyde, succinic anhydride, $SOCl_2$, or $R^1N=C=NR$.

Animals can be immunized against the immunogenic conjugates or derivatives by combining 1 mg or 1 μg of conjugate (for rabbits or mice, respectively) with 3 volumes of Freund's complete adjuvant and injecting the solution intradermally in multiple sites. One month later the animals are boosted with ⅕ to 1⁄10 the original amount of conjugate in Fruend's complete adjuvant by subcutaneous injection at multiple sites. Seven to 14 days later animals are bled and the serum is assayed for anti-noggin titer. Animals are boosted until the titer plateaus. Preferably, the animal is boosted with the conjugate of the same noggin polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by EB virus transformation and screening for clones expressing the desired antibody.

In a preferred embodiment, a rat monoclonal antibody such as RP57-16, prepared after immunization of a rat with recombinant human noggin, reacts specifically with both Xenopus and human noggin, but not with the neurotrophins BDNF, NT-3 and NT-4.

Noggin antibodies are useful in diagnostic assays for noggin or its antibodies. In one embodiment of a receptor binding assay, an antibody composition which binds to all of a selected plurality of members of the noggin family is immobilized on an insoluble matrix, the test sample is contacted with the immobilized antibody composition in order to adsorb all noggin family members, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

Noggin antibodies also are useful for the affinity purification of noggin from recombinant cell culture or natural sources. Noggin antibodies that do not detectably cross-react with other growth factors can be used to purify noggin free from these other family members.

Aspects of the invention will now be illustrated by the following examples.

EXAMPLES

Production of Xenopus embryos

Xenopus embryos were prepared by the protocol described by Condie and Harland (Development, 101, 93–105, 1987). Embryos were staged according to the table of Nieuwkoop and Faber ("Normal Table of Xenopus laevis" (Daubin), Amsterdam: North Holland, 1967). Ventralized embryos were produced by irradiation with a Statalinker (Stratagene), and dorsalized embryos were produced by treatment with LiCl as described by us in our paper on certain "wnt" proteins (designated "Xwnt-8"), Smith and Harland, Cell, Vol. 67, pp. 753–765 (1991) (incorporated by reference and occasionally referred to hereinafter as "S&H, supra").

Example 1

Isolation and Sequencinq of Noggin cDNA

The construction of the size-selected plasmid cDNA library from stage 11 LiCl-treated embryos was as follows. Sixty micrograms of poly(A) RNA from stage 11 LiCl-treated embryos was size fractionated on a 10% to 30% sucrose gradient in the presence of methylmercuric hydroxide. First strand cDNA was synthesized from 2 μg of the size-fractionated poly(A) RNAs primed with oligo(dT) oligonucleotide containing the recognition site for NotI. After synthesis of the second strand, cDNAs were treated with EcoRI methylase, ligated with EcoRI linkers, digested with EcoRI and NotI, and finally ligated to 125 ng of modified pGEM-5Zf(-) (Promega). The pGEM-5Zf(-) used here was modified by the addition of an oligonucleotide into the NsiI site to create an EcoRi site. The vector was not treated with alkaline phosphatase, but the excised polylinker sequence was removed on a sepharose 4BCL column. The ligated products were used to transform XL-I Blue cells (Stratagene), and plated to give 100,000 colonies per 10 cm plate. Plasmid DNAs were isolated from plate cultures by the alkaline-lysis/polyethylene glycol precipitation protocol.

Dorsalizing activity in the library was assayed by injecting RNA transcripts made from pooled plasmid DNA. Single clones were isolated by a process of sib selection. In this procedure the plasmid library was replated on 12 plates with 10-fold fewer colonies per plate. RNA was synthesized from pooled plasmid DNAs isolated from each plate and tested for dorsalizing activity by injection into UV-ventralized embryos. Those pools with dorsalizing activity were replated and screened as described above. This process was repeated until single clones were isolated.

In vitro RNA synthesis, injection assay for dorsal axis rescue and sib-selections were also done, as described by us in S&H, supra.

The nucleotide sequence of both strands of the isolated noggin cDNA clone was determined by the dideoxy termination method using modified T7 DNA polymerase (US Biochem). Deletions were prepared in sequencing templates by both restriction enzyme and exonuclease III digestion (Henikoff, Meth. Enzymol, 155, 156–165, 1987).

In vitro translation

One-half μg of in vitro synthesized noggin, Xwnt-8, and goosecoid mRNAs were translated in a nuclease treated rabbit reticulocyte lysate (Promega) with added $^{35}S$-methionine according to the manufacturer's instructions. The translation products were visualized by SDS-polyacrylamide gel electrophoresis (12% gels) followed by fluorography. Noggin protein had the molecular weight predicted by the open reading frame.

RNA Isolation and Analysis

Total RNA was isolated from embryos and oocytes by a small scale protocol as described by Condie and Harland, supra. Dorsal lips were dissected from 30 unfixed stage 10.5 embryos and pooled for total RNA preparation. Samples containing either the total RNA equivalent of 2.5 embryos or approximately 2 μg of poly A+ RNA were analyzed by northern blotting. Random primed DNA probes were prepared from a 1,323 bp fragment of noggin cDNA from the EcoRI site at nucleotide -83 to an EcoRV site that lies in the vector immediately 3' to the end of the cDNA.

RNAse protection assays were done using a protocol as detailed by Melton et al. (Nuc. Acids Res., 12, 7035–7056, 1984) with minor modifications (C. Kintner, Salk Institute, La Jolla, California). A noggin cDNA exonuclease III deletion clone, illustrated by Xenopus noggin but having a deletion from the 3' end to nucleotide 383, was used as a template for synthesizing RNA probes. The template DNA was linearized by EcoRI restriction enzyme digestion and a 463 base antisense RNA incorporating $^{32}$P was synthesized with T7 RNA polymerase. A 387 base antisense EFlα RNA probe was used as a control for amount of RNA per sample. Probes were gel purified prior to use.

In situ hybridization

After fixation and storage, the embryos were checked to ensure the blastocoel and archenteron were punctured. Care was taken to puncture the residual blastocoel of neurulae and tadpoles as well as the archenteron. Embryos were rewashed at room temperature in 100% ethanol for two hours to remove residual lipid. After hybridization, staining was allowed to develop overnight and the embryos were then fixed in Bouin's. Newly stained embryos have a high background of pink stain but most of this washes out, leaving the specific stain. Following overnight fixation, the embryos were washed well with 70% ethanol, 70% ethanol buffered with PBS and methanol. Embryos were cleared in Murray's mix and photographed with Kodak Ektar 25 film, using a Zeiss axioplan microscope (2.5 or 5× objective with 3×12B telescope to assist with focusing).

Lineage Tracing

Lineage tracing with mRNA that encodes nuclear localized B-galactosidase was as we described in S&H, supra. Ventralized embryos were coinjected at the 32 cell stage with 0.5 ng B-galactosidase and 25 pg nogginΔ5' mRNAs. Embryos were fixed and stained with X-gal at approximately stage 22.

Results

Noggin cDNA Encodes a Novel Polypeptide

The 1833 nucleotide sequence of the selected clone is insert Xenopus noggin and sometimes also referred to as "clone A3." The sequence contains a single long open reading frame encoding a 222 amino acid polypeptide with a predicted molecular weight of 26 kDa. At the amino terminus, the hydrophobic stretch of amino acids suggests that the polypeptide enters the secretory pathway. There is a single potential site for N-linked glycosylation at amino acid 61. Extensive untranslated regions are located both 5' and 3' to the reading frame (593 and 573 bp, respectively). The 3' untranslated region is particularly rich in repeated dA and dT nucleotides, and contains, in addition to a polyadenylation signal sequence located 24 bp upstream from the start of the poly A tail, a second potential polyadenylation sequence 147 bp further upstream.

Sense RNA synthesized from clone A3 with SP6 RNA polymerase was translated in a rabbit reticulocyte lysate system. The 3S-labeled products were fractionated on a 12% SDS-polyacrylamide gel and visualized by fluorography. The major protein product had the expected molecular weight of approximately 26 kDa.

Comparison of the amino acid sequence of the predicted polypeptide to the National Center for Biotechnology Information BLAST network (non-redundant data base) did not identify any similar sequence. Thus, this clone encodes the new type of protein we have named "noggin" which is secreted, and which has dorsal inducing activity in Xenopus.

Noggin mRNA can Rescue a Complete Dorsal-Ventral Axis

Injection of noggin RNA into a single blastomere of a four cell stage UV-ventralized embryo can restore the complete spectrum of dorsal structures. The degree of axis rescue was dependent upon the amount of RNA injected, with embryos receiving low doses having only posterior dorsal structures, while embryos receiving higher doses had excess dorsal-anterior tissue. RNA transcripts from two noggin plasmids were tested. The first contained the full cDNA. The second (pNogginΔ5') had a deletion removing the first 513 nucleotides of the 5' untranslated region up to the EcoRI site. The resulting embryos from injection of RNA transcripts of these two plasmids, as well as Xwnt-8 RNA for comparison, were scored according to the dorsoanterior index (DAI) scale of Rao and Elinson (Dev. Biol., 127, 64–77, 1988). In this scale, a completely ventralized embryo is scored as zero, a normal embryo is scored as 5, and the most severely dorsoanteriorized embryos, those having radial dorsoanterior structures, were scored as 10. RNA synthesized from pNogginΔ5' (nogginΔ5' mRNA) repeatedly gave a higher DAI than the equivalent amount of mRNA synthesized from the complete cDNA. The dose-dependency of axis rescue by nogginΔ5' mRNA was very similar to that of Xwnt-8 mRNA.

UV treated embryos were also injected with a higher doses (1,000 pg) of the noggin mRNAs. Injection of this dose of noggin mRNA into one blastomere at the four cell stage resulted in embryos with very severe hyperdorsalization (DAI>7). However, most of these embryos died at the late gastrula/early neurula stage. Apparently excessively strong gastrulation movements resulted in the thinning and rupture of the blastocoel roof. We have also observed this effect with high doses of injected Xwnt-8 mRNA.

The rescue of dorsal development by both nogginΔ5' and Xwnt-8 mRNAs followed a consistent pattern in which increasing amounts of the mRNAs lead to progressively more anterior structures being rescued. For example, embryos that received 1 pg of the RNAs had primarily the posterior and trunk dorsal structures rescued, and for the most part lacked head structures. Higher doses (10 or 100 pg) of both of the RNAs resulted in embryos with more anterior development, and many had either nearly normal or hyperdorsalized phenotypes.

Noggin Injected Blastomeres Act as a Nieuwkoop Center

The effect of varying the site of noggin mRNA injection was investigated. Thirty-two cell stage UV-treated embryos were injected with either 0.5 ng of B-galactosidase mRNA alone or 0.5 ng B-galactosidase mixed with 25 pg nogginΔ5' mRNA. Injection of noggin mRNA into blastomeres of the vegetal tier gave the most strongly dorsoanteriorized embryos. In both of the vegetal injected embryos the nuclear X-Gal staining was found almost exclusively in the endoderm (the mRNA encodes a B-galactosidase that translocates to the nucleus, allowing distinction from the diffuse background stain). One of the embryos shown was strongly hyperdorsalized (DAI approximately 7) as a result of the noggin mRNA injection, and had a severely truncated tail and enlarged head structures. Embryos were also rescued by noqgin mRNA injections into the marginal zone.

In these embryos B-galactosidase staining was observed primarily in the axial and head mesoderm. Injection of noggin mRNA into the animal pole had very little effect on axis formation. Likewise, B-galactosidase mRNA alone was without effect.

Noggin mRNA is Expressed Both Maternally and Zygotically

In northern blot analysis of RNA from Xenopus embryos two noggin mRNA species of approximate sizes 1.8 and 1.4 kb were observed. A relatively low level of noggin mRNA was detected in oocytes. By stage 11 the level of noggin mRNA was significantly higher, reflecting zygotic transcription (as opposed to the maternally deposited transcripts seen in oocytes). Noggin mRNA remained at the elevated level up to the latest stage examined (stage 45).

We expect that the primary dorsalizing RNA in our library to be elevated in LiCl-treated embryos relative to normal or UV-treated embryos. Lithium ion treatment resulted in a large increase in the amount of noggin mRNA expressed, relative to untreated embryos.

UV treatment had the opposite effect. Noggin mRNA expression was essentially undetectable in total RNA samples from these embryos. Thus, the abundance of noggin mRNA in manipulated embryos parallels the rescuing activity.

We analyzed the distribution of noggin in oocytes and cleavage stage embryos. Since the amount of maternally deposited noggin RNA is too low for in situ hybridization to detect above background, we used an RNAse protection assay. Oocytes were dissected into animal and vegetal halves. No enrichment of noggin mRNA was seen in either hemisphere relative to total oocyte RNA. Four-cell stage embryos were dissected into dorsal and ventral halves, as well as animal and vegetal halves. Noggin transcripts were found to be distributed evenly between dorsal and ventral hemispheres as well as animal and vegetal hemispheres. The same result was obtained with embryos that were tilted 90° immediately following fertilization and then marked with a vital dye on their uppermost side to indicate the future dorsal side. Older (32 cell stage) blastula embryos were also dissected into dorsal-ventral and animal-vegetal halves. No enrichment of noggin mRNA in any of the hemispheres was seen relative to the total embryo. In addition, treatment did not alter the abundance of maternally deposited noggin RNA, indicating no preferential degradation in ventral tissues. Samples with known amounts of in vitro synthesized noggin mRNA were included in the RNAase protection assay. From these and other data we estimate that there is approximately 0.1 pg of noggin mRNA per blastula stage embryo and 1 pg per gastrula stage embryo.

The localization of noggin transcripts was investigated in early gastrula stage embryos. Dorsal lips were dissected from stage 10.5 embryos. A northern blot of equal amounts of total RNA from intact embryos, dissected dorsal lips, and from the remaining embryo after dissection of the dorsal lip was hybridized with a noggin probe and then re-hybridized with an EFla probe, as a control for amount of RNA loaded per sample. The autoradiograph of the blot showed that noggin mRNA at this stage is enriched in the dorsal lip.

In situ Hybridization: Zygotic Expression of Noggin in the Spemann Organizer

The localization of noggin transcripts in developing embryos was examined in greater detail using whole mount in situ hybridization. Whole fixed embryos were hybridized with digoxigenin containing RNA probes.

Hybridized RNA probe was then visualized with an alkaline phosphatase-conjugated anti-digoxigenin antibody. The specificity of hybridization seen with antisense noggin probes was tested both by hybridizing embryos with sense noggin probes, and by using two non-overlapping antisense probes. Due both to the low level of expression, and to background staining, noggin mRNA could not be detected unequivocally before the late blastula stage. The increased level of noggin mRNA that was detected by northern blot following activation of zygotic transcription was apparent in in situ hybridization at stage 9 as a patch of staining cells on the dorsal side of the embryo. Viewed from the vegetal pole, this patch of cells was restricted to a sector of about 600. A side view of the same embryo shows that the staining cells were located within the marginal zone (i.e., between the animal and vegetal poles and within the presumptive dorsal mesoderm forming region). Transcripts are largely restricted to the nucleus at this stage.

A side view of an early gastrula stage embryo 30 (approximate stage 10.5) shows specific hybridization primarily in the involuting mesoderm at the dorsal lip. A vegetal view of the same embryo (blastopore lip arrowed) shows that noggin mRNA is most abundant on the dorsal side, but expression extends at the lower level to the ventral side of the embryo. This method of in situ hybridization does not detect transcripts in the most yolky endodermal region of embryos, therefore we cannot rule out expression in more vegetal regions than those seen in the Figure. Treatments which are known to affect the size of the dorsal lip (LiCl treatment, UV irradiation) had a profound effect on the pattern of noggin in situ hybridization. In LiCl treated embryos the staining is intense throughout the marginal zone. UV treatment reduced the hybridization signal to low levels. This result is consistent with amounts of noggin mRNA seen by northern blot analysis. The UV treated embryo also is a negative control for specificity of hybridization.

As gastrulation proceeds, noggin mRNA staining follows the involuting dorsal mesoderm, and is highest in the presumptive notochord. By the late neurula stage (approximately 18) noggin mRNA expressing cells are clearest in the most dorsal mesoderm, primarily in the notochord but also extending more anteriorly into the prechordal mesoderm. The anterior tip of the notochord is arrowed. During tailbud stages expression of noggin in the dorsal mesoderm declines, through expression in the notochord persists in the growing tailbud. Expression of noggin initiates at several new sites, which become progressively clearer as the tadpole matures. A discontinuous line of stained cells runs the length of the roof plate of the neural tube. Staining is also apparent in the head mesoderm, primarily in the mandibular and gill arches. We suspect that this expression corresponds to skeletogenic neural crest cells. Furthermore, subsets of these cells express homeobox genes that mark different anterior-posterior levels of the head neural crest, for example En-2 in the mandibular arch is seen by antibody staining. Cells with stellate morphology stained from noggin mRNA in the tail fin. These stellate cells are also likely to be derived from the neural crest. None of these patterns were seen with the sense probe, or with a number of other probes.

Example 2

Noggin cDNA Transfected into COS Cells Produces Active Conditioned Medium

For COS cells the noggin cDNA was inserted into a COS cell expression vector. COS cells were transfected, and medium harvested after allowing expression of the introduced noggin genes. This medium has been tested in an animal cap assay for mesoderm inducing or dorsalizing activity. We have tested two transfection protocols, a standard one, where cells recover and then are transferred to serum-free medium, and an alternate where cells are transferred to a defined medium lacking serum but containing transferrin, insulin, and BSA. Cells remain healthy in the supplemented medium and a cotransfected β-galactosidase gene gives 100 fold more activity than in the unsupplemented medium. The results of treating cells with these media is shown below in Table 1. Animal caps were taken from ventralized animals, treated and at the end of neurulation they were scored for elongation, usually a sign that notochord or neural tissues have been induced. Elongation is indicated in Table 1 by a "+" and even greater elongation a "++." In addition, they are scored for a molecular marker by Northern blotting.

As shown by the data of Table 1, the noggin cDNA has a large effect on the COS cell conditioned medium. However, noggin is probably interacting with something else in the medium, since COS-cell conditioned medium alone has some activity. It is possible that noggin is causing the cells to secrete something that they normally would not, but the experiments do indicate that noggin is secreted and is responsible for some of the activity.

TABLE 1

Cos Cell Conditioned Medium: Effects on Animal Caps

|  | Elongation | N-CAM expression |
|---|---|---|
| Transferred to serum free medium + transferrin, BSA, and insulin | | |
| 1. Vector only | +/− | + |
| 2. Noggin cDNA | ++ | ++ |
| Transferred to serum free medium without supplements | | |
| 1. Vector only | − | − |
| 2. Noggin cDNA | − | − |

Noggin mRNA Injected into Oocytes Produces Active Secreted Noggin Protein

A second approach to studying whether protein can be secreted in active form is to inject oocytes with mRNA and take material secreted by the oocyte. A particular advantage of this method is that the injected mRNA is efficiently translated, and most of the translation of the oocyte can be taken up by the injected mRNA. A new protein, whose synthesis is directed by injected noggin mRNA is secreted into the medium. Noggin clearly synergizes with activin to produce elongated explants that express elevated levels of muscle actin.

Biochemical Properties of Noggin

Injected oocytes are injected with mRNA, and labelled with $^{35}S$ methionine. Most of the radioactive protein secreted into the medium is from the injected mRNA. The noggin protein, which is almost isotopically pure, can then be analyzed. From this analysis we have determined that noggin is a dimeric glycoprotein. When run under reducing conditions, and treated with N-glycanase to remove sugar residues, noggin migrates only slightly slower than its predicted molecular weight of 26 kDa. The removal of sugar side chains results in a loss of about 4 kDa from a starting apparent molecular weight of 33 kDa. When run under non-reducing conditions it migrates at double this value.

We do not yet know if the dimer of the protein is the active species, or if there is a proteolytically processed form which is active. In a control experiment with activin mRNA, oocytes produce activin activity, but the bulk of the radiolabelled protein migrates as the precursor form. Only a small amount of processed protein (15 kDa) was detected. It is possible that noggin injected oocytes secrete predominantly unprocessed protein and a trace of extremely active processed protein that we have not detected. Despite the caveats, the main point from analysis of injected oocytes and transfected COS cells is that active noggin can be obtained as a freely soluble secreted polypeptide. This sets it apart from the other group of genes with dorsalizing activity, the wnts. Wnt proteins have not been available in soluble form and this has greatly hampered the analysis of their biological activities, and of the receptor that binds to them.

Example 3
Cloning of the Mouse Noggin Homolog

It is currently impossible to eliminate zygotic noggin transcription from developing Xenopus embryos. In contrast, it should be possible to generate homozygous null mutations in the mouse. We have cloned the partial mouse noggin cDNA. This is useful to generate mutant mice. In addition to generating the probes and tools to make mutant mice, a comparison of the noggin sequences should be a useful predictor of conserved domains and functions. The C-terminal 80 amino acids are 87% identical between Xenopus noggin and partial mouse noggin.

Mouse noggin was isolated from an embryonic cDNA library by probing with a radiolabelled frog noggin cDNA under conditions of moderate stringency (as defined earlier). Subsequently a genomic clone was isolated by probing a genomic library with the mouse noggin cDNA under conditions of high stringency (as defined, but hybridized at 42° C. and washed at 50° C. in 15 mM NaCl, 1.5 mM sodium citrate). The full nucleotide sequence of mouse noggin cDNA (SEQ ID NO: 10) as well as the deduced amino acid sequence (SEQ ID NO: 11) are shown in FIGS. 13A–13B. There are only two amino acid differences between mouse noggin and human noggin.

Example 4
Cloning of the Human Noggin Homolog
Materials and Methods
Probe preparation Two oligonucleotides were synthesized based on the mouse noggin sequence (supra). The sequence of the oligonucleotides is noggin

5': 5'-CAG ATG TGG CTG TGG TCA-3' (SEQ ID NO: 18)

corresponding to amino acids

QMWLWS (SEQ ID NO: 19)

and noggin

3': 5'-GCAGGAACACTTACACTC-3' (SEQ ID NO: 20)

corresponding to amino acids

ECKCSC (SEQ ID NO: 21)

of the mouse noggin protein.

The oligonucleotides were used for PCR amplification of a segment of DNA of 260 nucleotides using as a template a mouse cDNA clone prepared as set forth in Example 3. The amplified fragment had a nucleotide sequence that corresponds to nucleotides 2 through 262 of the partial mouse noggin sequence as set forth in SEQ ID NO: 10 as set forth in SEQ ID NO: 10. After amplification, the PCR reaction was electrophosed in agarose gels, the DNA band of 260 nts purified by Magic PCR (Promega), and used as template for the probe labeling reaction. The probe was labeled using a standard PCR reaction (Perkin-Elmer) on 20 ng of DNA template and 0.2 m Curie of alpha 32P-dCTP (Du Pont 3000 Ci/mmol) instead of dCTP. Unincorporated label was separated from the probes on a G50 NICK column (Pharmacia). The excluded volume of the reaction contained a total of 1.8×108 cpm.

In addition, one degenerated oligonucleotide, named noggin D, corresponding to conserved mouse and Xenopus noggin sequences, was synthesized as follows: Noggin D: 5'-GARGGIATGGTTTGYAARCC-3' (SEQ ID NO: 22). Noggin D (SEQ ID NO: 22) was labeled by kinase reaction using T4 polynucleotide kinase and gamma 32P ATP. The labeled oligonucleotide was purified by NAP5 (Pharmacia) column and used for library hybridization.

Library screening

A human placental genomic library (Clontech Cat#HL1067J, average insert size 15 kb) in vector EMBL-3 was plated according to manufacturer specifications in NM 538 *E.coli*. Approximately 3 million plaques were transferred to nitrocellulose filters (BA-85 Schleicher and Schuell) in three replicas (named A, B and C) and screened according to Maniatis, et al.[Sambrook, et a., Molecular cloning a laboratory manual, CSH Lab Press, New York (1989)]. The replica filters A and C were hybridized in a buffer containing 0.5 M sodium phosphate, pH 7.2, 7% sodium dodecyl sulphate, 1% crystalline BSA, 1 mM EDTA, 40 m g/ml denaturated salmon sperm DNA and about 1×106 cpm/ml of the PCR probe (supra). After hybridization for 12 h at 65° C., the filters were washed twice at room temperature in 2× SSC (30 mM sodium citrate, 0.3 M NaCl), 0.1% SDS and then at 65° C. in 2× SSC, 0.1% SDS for 20 min and exposed to Kodak X-OMAT AR film. The filter replica B were hybridized with the labeled oligonucleotide noggin D in 6× SSC, 0.1% SDS at 51° C. for 12 h followed by wash at 2× SCC, 0.1% SDS at room temperature, and in 6× SSC, 0.1% SDS at 50° C. and exposed to Kodak X-OMAT AR film. Positive plaques from all replicas were isolated and purified by re-screening as above. Purified positive plaques were suspended in 500 µl SM (100 mM NaCl, 10 mM MgSO4×7H20, 50 mM Tris HCl pH 7.5, 0.01% gelatin). 160 µl of phage suspension was mixed with 0.5 ml saturated NM538 culture, incubated for 20 min at 37° C. and then inoculated into 250 ml LB containing 10 mM Mg SO4, 0.2% maltose. The cultures were incubated until cell lysis (7–8 hr) at 37° C. The phage lysates were used for phage DNA purification by the Qiagen procedure according to the manufacturers recommendations (Qiagen).

Sequencing

Sequencing was performed by using the Applied Biosystems Model 373A automatic sequencer and Applied Biosystems Taq DyeDeoxy™ Terminator Cycle Sequencing Kit.

Results

Filters hybridized to the PCR mouse noggin probes (SEQ ID NOS: 18 and 20) showed two strong signals corresponding to phage plaques named hnogλ-9 and hnog-10. These plaques also hybridized to degenerate oligonucleotide probe nogginD (SEQ ID NO: 22) revealed that these clones correspond to the human noggin gene. In addition, two other plaques named hnogλ-5 and hnogλ-7 produced slightly weaker signals when hybridized to the PCR probes. These clones correspond to either human noggin or related gene(s). All of the human DNA inserts can be excised from the vectors using known restriction sites as described in the literature regarding each particular library.

A 1.6 kb SacI fragment from clone hnogλ-9 containing the human noggin gene was subcloned and the nucleotide sequence determined as set forth in FIGS. 1A–B (SEQ ID NO: 1). The amino acid sequence for human noggin, as deduced from the nucleotide sequence, is also set forth in FIGS. 1A–1B (SEQ ID NO: 2). The gene or cDNA may be expressed in various eukaryotic or prokaryotic expression systems to produce biologically active human noggin protein. It is expected that the human protein will exhibit neurotrophic activity similar to that exhibited by Xenopus noggin protein.

Example 5

Tissue Localization of message for human noggin

Materials and Methods

Probe preparation

Probes were prepared as set forth in Example 4. The oligos used are as follows:

SEQ ID NO: 8: 5' GAC.TCG.AGT.CGA.CAT.CG
C.AGA.TGT.GGC.TGT.GGT.CAC

SEQ ID NO: 9: 5' CCA.AGC.TTC.TAG.AAT.TC
G.CAG.GAA.CAC.TTA.CAC.TCG.G (The underlined sequence represent mouse noggin sequence; the rest of the sequence are tails containing restriction sites for cloning.)

A DNA fragment of approximately 300 bp was obtained by PCR amplification of a mouse cDNA clone prepared as described in Example 3.

RNA Preparation and Northern Blots

Selected tissues were dissected from Sprague-Dawley rats and immediately frozen in liquid nitrogen. RNAs were isolated by homogenization of tissues in 3 M LiCl, 6 M urea, as described in Bothwell, et al. 1990 (Methods of Cloning and Analysis of Eukaryotic Genes, Boston, MS, Jones and Bartlett). RNAs (10 µg) were fractionated by electrophoresis through quadruplicate 1% agarose-formaldehyde gels (Bothwell, et al., 1990, Methods of Cloning and Analysis of Eukaryotic Genes, Boston, MS, Jones and Bartlett) followed by capillary transfer to nylon membranes (MagnaGraph, Micron Separations Inc.) with 10× SSC (pH7). RNAs were UV-cross-linked to the membranes by exposure to ultraviolet light (Stratalinker, Stratagen, Inc.) and hybridized at 68° C. with radiolabled probes in the presence of 0.5 M NaPO$_4$ (pH 7), 1% bovine serum albumin (fraction V, Sigma, Inc.) 7% SDS, 1 mM EDTA [Mahoudi, et al., Biotechniques 7:331–333 (1989)], 100 µg/ml sonicated, denatured lo salmon sperm DNA. Filters were washed at 68° C. with 3× SSC, 0.1% SDS and subjected to autoradiography for 1 day to 2 weeks with one or two intensifying screens (Cronex, DuPont) and X-ray film (AR-5, Kodak) at 70° C. Ethidium bromide staining of the gels demonstrated that equivalent levels of total RNA were being assayed for the different samples [as in Maisonpierre, et al., Science 247:1446–1451 (1990)].

RNA was prepared from the following human cell lines:

| Neuroblastoma | Neuroepithelioma | Hematopoetic |
|---|---|---|
| CHP-134 | SK-N-MC | K562 |
| LA-N-1 | CHP-100 | U937 |
| LA-N-5 | IARC-EWI | M1 |
| IMR-32 | SK-N-LO | TF1 |
| SHSY5Y | SK-ES | BAF |
| SKNSH | DADY | B9 |
| SHEP | | |

| Small Cell Lung Carcinoma | Cervical Carcinoma | Sympathoadrenal Precursor |
|---|---|---|
| Calu 3 | HeLa | MAH |
| SKLu | | |
| NCI-H69 | | |
| SKMES | | |

| Hepatoblastoma | Medulloblastoma | Pheochromocytoma |
|---|---|---|
| HEPG2 | Madsen | PC12 |
| | Med | |
| | U266 | |

Results

We have amplified a DNA fragment from the mouse noggin plasmid, corresponding to the region conserved between Xenopus and mouse noggin.

The amplified fragment of approximately 300 bp was used as probe to hybridize to northerns, with RNAs prepared from adult and embryonic tissues, as well as from various cell lines. Noggin transcript of about 2 kb in size was detected in adult rat brain, and in a cell line, SKMES, a small cell lung carcinoma.

Expression of noggin transcripts was examined in various tissues from rat and mouse at different stages of development and in adult. In the mouse, noggin transcripts can be detected in embryos or head from E9 to E12, as well as in newborn brain and adult brain. There was no detectable signal in peripheral tissues examined except in skeletal muscle. Abundant level of expression was also found in hippocampal astrocytes isolated from postnatal mouse.

In the rat, noggin transcripts were detectable in embryos or head from E9 to E18, as well as in brain from P1, P19 and adult brain. In the cerebellum, expression of noggin appeared to be higher in E18 and P1; in the spinal cord, expression of noggin mRNA peaked at P1. Examination of noggin expression in all of the CNS regions, especially the olfactory bulb, midbrain, hindbrain and cerebellum. In the adult, noggin mRNA could be detected in all CNS regions, especially the olfactory bulb and cerebellum. There also appeared to be low levels in the skin.

Example 6

Neural Induction by Noggin

Materials and Methods

Preparation of Xenopus noggin CHO cell conditioned medium

Xenopus noggin CHO conditioned medium was made by selecting for stably transfected CHO cells. Dihydrofolate reductase (DHFR) deficient CHO parental cells (J. Papkoff, Syntex Research) were transfected with a Xenopus noggin expression plasmid containing noggin in tandem with the dihydrofolate reductase gene. Growth in nucleoside free medium was used to select for successfully transfected cells. Nine colonies of transfectants were picked and grown up individually. The noggin gene in these cells was amplified by slowly increasing the dose of methotrexate, an inhibitor of DHFR. The presence of noggin transcripts was first tested by Northern analysis. Subsequently, two clones, B3 and C3, were shown to secrete noggin protein, since conditioned medium from these lines was capable of dorsalizing ventral marginal zones. Furthermore, by labeling B3 cellular proteins with 35S-methionine, noggin protein could be identified as a band of about 30 kD on reducing SDS-PAGE, and a band of 60 kD on non-reducing SDS-PAGE indicating it forms the expected dimer. These properties matched those of the noggin protein previously produced in Xenopus oocytes supra, (Smith et al., Nature 361, 547–49, 1993). B3 conditioned medium was collected in a mixture of 1 part alpha MEM and 9 parts CHO-S-SFMII (Gibco-BRL). The cells were allowed to condition the medium for 3 days. Control medium from parental cells (CHO dhfr-) was collected identically. Twenty fold concentrated medium was made using Centriprep 10 concentrators, where the 20 fold change is measured by volume.

Purification of human noggin from COS cells

Human noggin protein was purified by a cationic exchange column.

COS/M5 cells were transiently transfected with a human noggin expression plasmid, pCAE11. Cells were allowed to condition DMEM (Specialty Media) for two to three days, after which the medium was removed. Particulates from the medium were removed by a centrifugation step and subsequent passage through a 0.2 um cellulose acetate filter. This cleared medium was pumped onto a MonoS (Pharmacia) column which was washed with several volumes 40 mM sodium phosphate (pH 7.3), 150 mM NaCl, 1 mM EDTA. Proteins were then eluted in a linear gradient with 40 mM sodium phosphate (pH 8.5), 1.8M NaCl, 1 mM EDTA. Noggin protein elutes at 0.8M NaCl and is ≧90% pure by SDS-PAGE.

Xenopus otx isolation

To isolate Xenopus Otx clones a tadpole head cDNA library (Hemmati-Brivanlou, et al., Development 106, 611–617, 1989) was screened with a mouse otx cDNA (S-L Ang and Rossant, Toronto) at low stringency. The clones that were picked fell into two classes. One class, which we have designated otxA, included pXOT21.2, the probe used here. By in situ hybridization, transcripts are first detected prior to gastrulation in the superficial layer on the dorsal side. During neurulation a large anterior domain expressed the gene, and includes both neural and non-neural tissues. After a decline in expression in the tailbud tadpole, the gene is reexpressed specifically in the brain and eyes.

Ventral marginal zone assay

Embryo preparation

Xenopus laevis embryos are fertilized and de-jellied as described (Condie and Harland, 1987. Development 101, 93–105), routinely the evening before dissections. Embryos are cultured overnight at 15° C. The vitelline membrane surrounding each developing embryo is manually removed the following morning at the late blastula stage. Until dissection, the embryos are maintained in ⅓× modified ringers in agarose coated dishes.

Ventral marginal zone dissection

Embryos are oriented with their yolky vegetal hemisphere up so the dorsal side can be identified. The dorsal side of the early gastrula is marked by the presence of a small arc of dense pigment called the "dorsal lip" which marks the start of involution of dorsal mesoderm. The ventral marginal zone (VMZ) is found directly opposite the dorsal lip, and is dissected. Since the vitelline membrane has been removed, the embryo tends to flatten. Using a specially constructed knife made of an eyebrow, mounted onto a glass pipet with wax, two cuts are made through the flattened embryo from the top facing vegetal pole through to the animal pole. The cuts are made such that they isolate approximately 30–60 degrees of the ventral side away from more lateral tissues. A third cut which is perpendicular to the first two cuts completely isolates the ventral marginal zone tissue away from the rest of the embryo. This third cut is at the level of approximately two thirds of the radius of the embryo from the center. Prior to treatment the VMZ is washed 1× in the culture medium.

Assay

Approximately between 5 to 10 VMZs are used per assay. The washed VMZs are dropped gently (trying to minimize transfer of liquid) into eppendorf tubes containing the desired treatment protein medium for assay. The VMZs are allowed to develop to the late neurula or early tailbud stage as assessed by control whole embryo development. At this time RNA is isolated from the VMZs and control whole embryos as described (Condie and Harland, ibid). The expression of muscle actin in VMZs indicates a dorsalization event (Lettice and Slack, 1933. Development, 117, 263–72). RNA from each sample is run on a formaldehyde-agarose gel and blotted to gene screen. The blot is then hybridized with a Xenopus muscle actin probe (Dworkin- Rastl et al., 1986. J. Embryol. exp. Morph. 91, 153–68). Quantitation of dorsalization can be carried out by normalizing muscle actin signal to that of the ubiquitously expressed EF-1α (Krieg et al., 1989. Devl. Biol. 133, 93–100). Quantitation is done using phosphor imaging.

RNase protection assay

RNase protection was carried out as described (D. A. Melton et al., Nucleic Acids Res 12,7035–56, 1984), with the modification that digestion was carried out at room temperature (22° C.) using RNase Ti only (Calbiochem 556785) at 10 units/mi. 20–30 animal caps were harvested for each lane, of this 80% was used for neural markers and 10% for muscle actin and collagen type II. For goosecoid and brachyury 20 caps were used. Exposures ranged from 12 hours to 5 days. In all cases, films were preflashed. In cases where a marker was not expressed, the result was confirmed with greater sensitivity using phosphor imaging.

Results

The development of vertebrate embryos requires several inductive interactions. Mesoderm, which eventually forms tissues such as notochord, muscle, heart, mesenchyme and blood, is induced in the equatorial region of the embryo (Nieuwkoop, Wilhelm Roux' Arch. EntwMech. Org, 162, 341–373, 1969). This inductive event is well studied, and there are several candidates for the endogenous inducer(s) including members of the fibroblast growth factor(FGF) family and activin (Jessell and Melton, Cell 68, 257–70 1992; Sive, Genes Dev 7, 1–12, 1993) and TGFb family (Asashima, et al., Roux's Arch. Dev. Biol. 198, 330–335, 1990; Asashima, et al., Naturwissenschaften 77, 8, 389–91, 1990; Green and Smith, Nature 347, 391–394, 1990; Smith, et al., Nature 345, 6277, 729–31, 1990; Thomsen, et al., Cell 63, 485–493, 1990; van, et al., Nature 345, 6277, 732–4, 1990). The use of dominant negative receptors for both FGF (Amaya, et al., Cell 66, 257–270, 1991) and activin (Hemmati-Brivanlou and Melton, Nature 359, 609–614, 1992) in Xenopus embryos strongly suggests that the signaling pathways activated by these molecules are essential for proper mesoderm formation. Molecules such as wnts (Christian, et al., Development 111, 1045–1055, 1991; McMahon and Moon, Cell 58, 1075–84, 1989; Smith and Harland, Cell 67, 753–765, 1991; Sokol, et al., Cell 67, 741–752, 1991) and noggin (Smith, et al., Nature 361, 547–49, 1993) modify the kinds of mesoderm made without inducing mesoderm directly.

In a subsequent induction, the dorsal mesoderm of the Spemann organizer signals nearby lateral mesoderm to take on a more dorsal fate (Dale and Slack, Development 100, 2, 279–95, 1987; Lettice and Slack, Development, 117, 263–271, 1993; Spemann and Mangold, Arch. mikrosk. Anat. EntwMech. 100, 599–638, 1924; Stewart and Gerhart, Development 109, 363–372, 1990). The only known factor which is expressed in the organizer and can mimic its dorsalizing activity is noggin.

Dorsal mesoderm of the Spemann organizer also signals nearby ectoderm to become neural tissue. Neural induction by dorsal mesoderm has been demonstrated in amphibians (Dixon and Kintner, Development 106, 749–757, 1989; Doniach, et al., Science 257, 5069, 542–5, 1992; Hamburger, The Heritage of Experimental Embryology: Hans Spemann and the Organizer, 1988; Kintner and Melton, Development 99, 311–25, 1987; Spemann, Arch. mikrosk. Anat. EntwMech. 100, 599–638, 1938), birds (Kintner and Dodd, Development 113, 1495–1506, 1991; Tsung, et al., Acta Biol exp Sinica 10, 69–80, 1965), and recently in mice (Ang and Rossant, Development 118, 139–149, 1993). Despite decades of effort, little is known about the molecular nature of the factors responsible for this induction. Among known inducers, activin can promote formation of neural tissue, but this is due to a secondary induction by the dorsal mesoderm that activin induces (Green, et al., Development 108, 1, 173–83, 1990; Green and Smith, Nature 347, 391–394, 1990; Kintner and Dodd, Development 113, 1495–1506, 1991). Thus, activin cannot promote formation of neural tissue when added to gastrula ectoderm; however, such ectoderm remains competent to be neuralized by dorsal mesoderm until the end of gastrulation (Sharpe and Gurdon, Development 109, 765–74, 1990).

Direct Neural Induction by Noggin

Candidates for the endogenous inducer are expected to induce neural tissue in the absence of dorsal mesoderm. Competent animal cap ectoderm from late blastula stage embryos (St9) was used to test noggin's neural inducing capacity. Xenopus noggin protein conditioned medium was collected from stably transfected CHO cells and twenty fold concentrated medium was used to treat St 9 animal caps. Markers used in an RNase protection assay were N-CAM (Jacobson and Rutishauser, Developmental Biology 116, 524–31, 1986; Kintner and Melton, Development 99, 311–25, 1987), a neural cell adhesion molecule, a neural specific isoform of b-tubulin (Good, et al. Nucleic Acids Res 17, 8000, 1989; Good, et al., Dev Biol 137, 414–8, 1990; Richter, et al., Proc Natl Acad Sci USA 85, 8086–90, 1988) that is expressed in the hind brain and spinal cord, and XIF3, a neurally expressed intermediate filament gene (Sharpe, et al., Development 107, 701–14, 1989) to assay for neural induction. All these markers are restricted to neural tissue, however, only NCAM is expressed throughout the nervous system. We found that Xenopus-noggin conditioned medium induces high levels of N-CAM and XIF3 expression[FIG. 2.; lane8] in treated animal caps, without inducing muscle actin(lane 13) (Dworkin-Rastl, et al., J. Embryol. exp. Morph. 91, 153–168, 1986; Mohun, et al., Nature 311, 716–721, 1984). Control CHO cell medium induces neither muscle nor neural tissues (lanes 7,12). St 9 activin treated animal caps express muscle actin(lane11) and all three neural markers(lane 6), demonstrating activin's ability to generate neural tissue indirectly. It is interesting to note that noggin induces very little, if any b-tubulin expression, while inducing high levels of N-CAM, but activin induction has nearly the converse effect.

Figure 3:
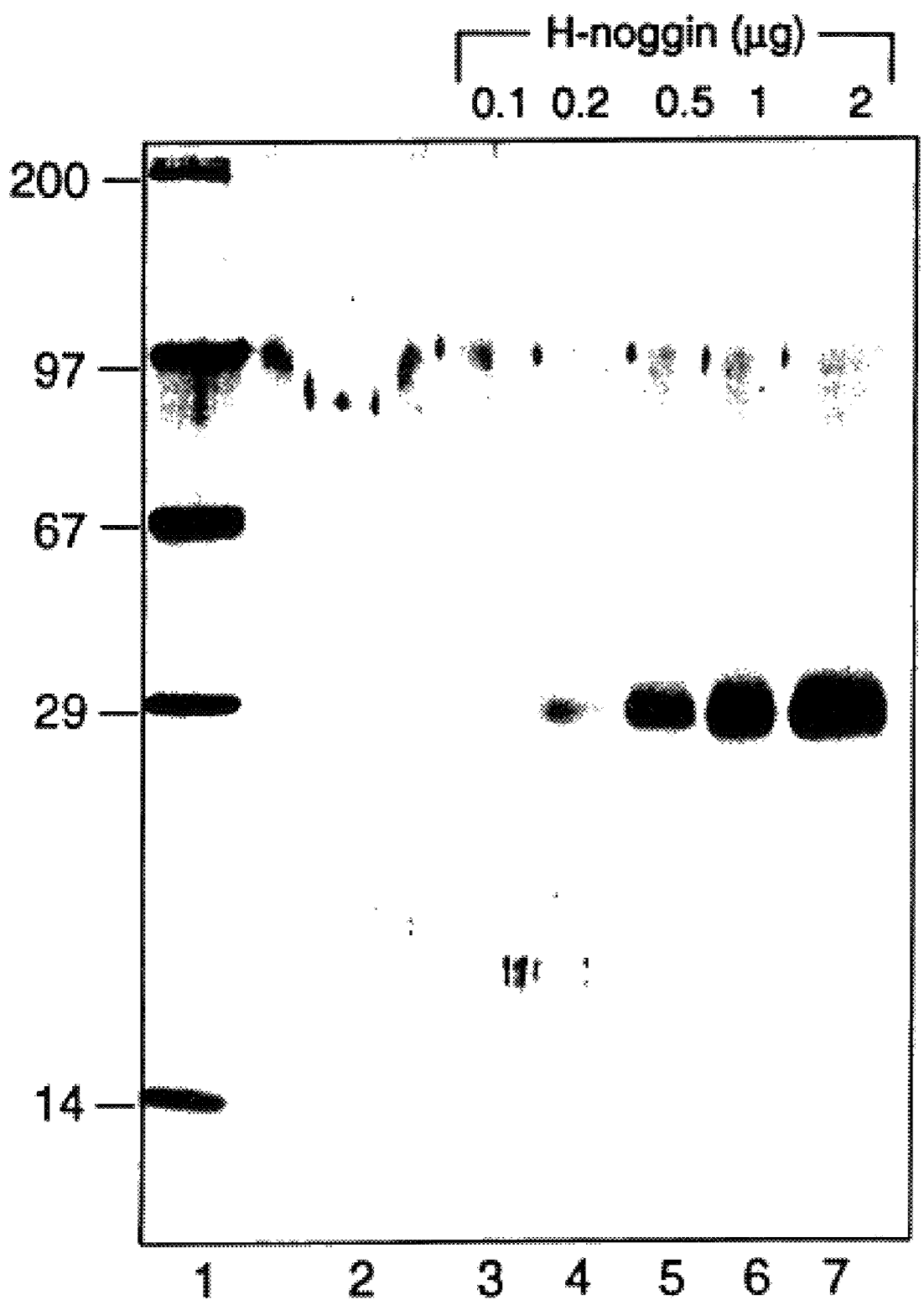
FIG. 3—SDS-PAGE (12%) run under reducing conditions. Proteins were visualized by silver staining. Lane 1 shows molecular size standards. Lanes 2–7 show 0.0, 0.1, 0.2, 0.5, 1.0 and 2.0 μg of purified human noggin.
Figure 4A:
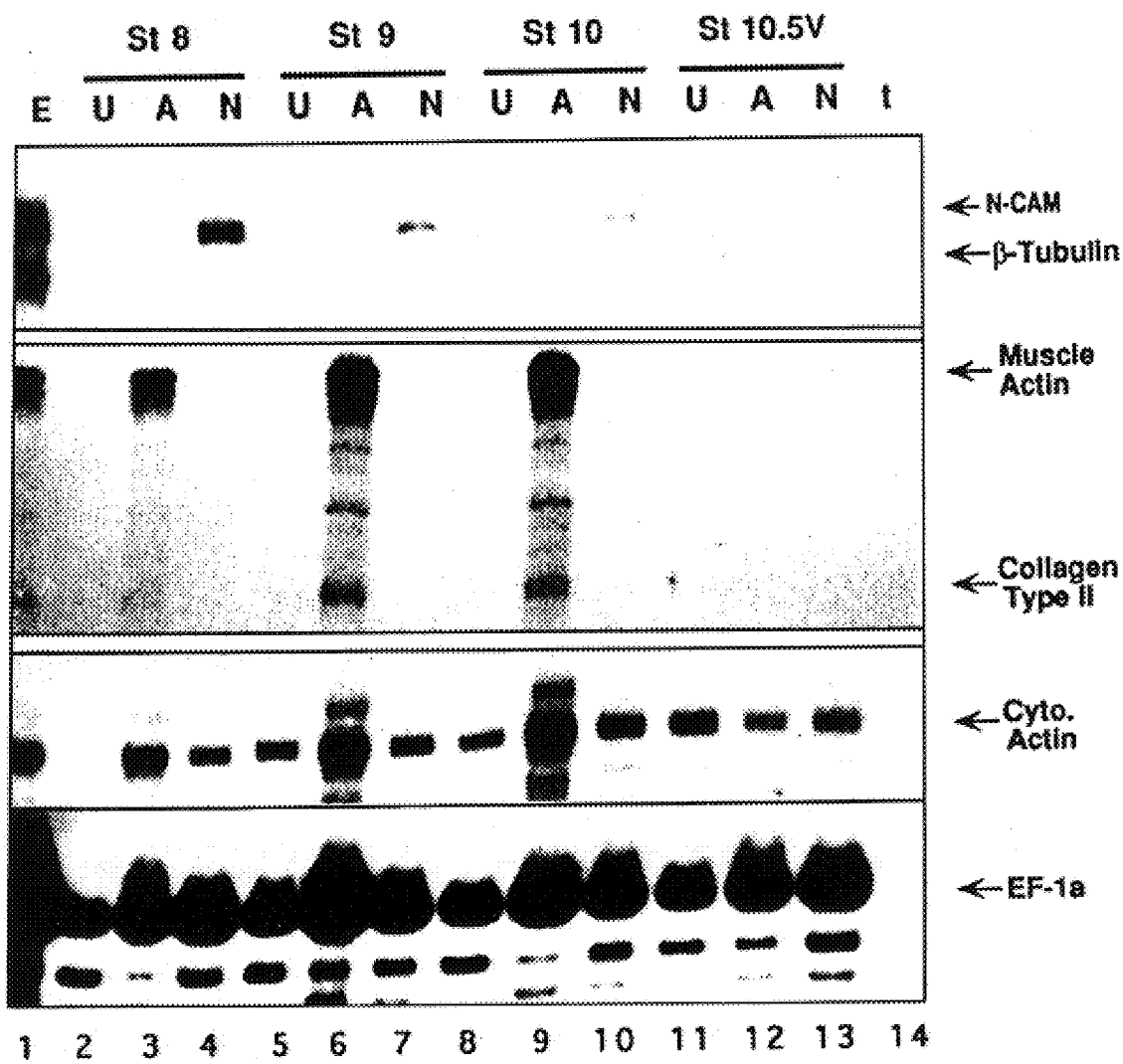

To determine whether noggin protein is sufficient to induce neural tissue, COS cells were transfected with pCAE11, a human noggin expression plasmid, and the conditioned medium was purified by cation exchange chromatography resulting in noggin preparations that were 90% pure [FIG. 3.]. Such purified human noggin protein is also able to induce neural tissue in animal caps [FIG. 4a., see below].

We have shown that noggin does not induce muscle in late blastula stage animal caps, however, it is possible that noggin induces other types of dorsal mesoderm. To address this concern, we asked whether noggin could induce the expression of the early mesoderm markers goosecoid (Blumberg, et al., Science 253, 194–6, 1991; Cho, et al., Cell 67, 1111–20, 1991), a marker of organizer tissue and subsequently head mesoderm or X-brachyury (Smith, et al., Cell 67, 79–87, 1991 ), which appears to be expressed in all mesodermal precursors early, and subsequently is expressed in posterior mesoderm and notochord. Animal caps were treated at stage 9 and collected at stage 11, when expression of goosecoid and brachyury in the normal embryo is high. Neither marker is turned on by purified human noggin (FIG. 4b. lane 5) at a dose with demonstrated neural inducing activity (FIG. 6 lane15); in contrast animal caps treated in the same fashion with activin show both goosecoid and X-bra expression (FIG. 4b. lane 4) as expected for this mesoderm inducing factor (Cho, et al., Cell 67, 1111–20, 1991; Smith, et al., Cell 67, 79–87, 1991). Untreated animal caps show no expression of these mesodermal markers (lane 3), and RNA levels in the collected animal caps are shown to be comparable using EF-1a levels (Krieg, et al., Dev Biol 133, 93–100, 1989).

Since purified human noggin is capable of driving neural induction, no additional factors which may have been present in the crude conditioned medium are required. Furthermore, Xenopus and human noggin, with 80% amino acid identity, can both act to induce neural tissue in Xenopus, suggesting a conserved function for these two proteins. However, for noggin to be a candidate endogenous neural inducer it must be able to induce neural tissue at a stage when neural induction occurs in normal whole embryos. It is unclear when the first instructive signals are sent from dorsal mesoderm to ectoderm in embryos. However, it is known that by early gastrula stages, dorsal ectoderm has already been specified to become neural tissue (Jones and Woodland, Development 107, 785–91, 1989). The neural inducing signal is therefore likely to start before this stage. The latest stage at which animal caps have been shown to be competent to respond to neural-inducing mesoderm is the early neurula (St13–14) (Sharpe and Gurdon, Development 109, 765–74, 1990). Thus, a candidate endogenous neural inducer must be able to induce neural tissue from gastrula stage competent ectoderm.

Neural Induction at the Gastrula Stage

Figure 2A:
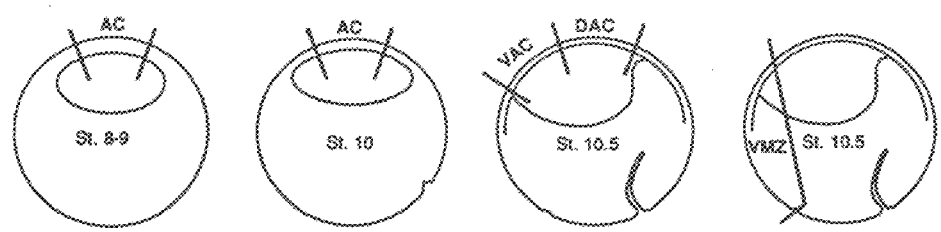
FIG. 2A—Experimental design: competent animal cap (AC) ectoderm was dissected from staged embryos as shown. St10.5 dorsal and ventral AC and ventral marginal zones (VMXZ) also dissected as shown. Explants were washed once in low Ca/Mg Ringers (LCMR) solution and then placed in treatment medium containing factor diluted in LCMR+0.5%BSA. Explants cultured to late stages (St20+) were removed from treatment medium 6–16 hours after the start of treatment and placed in LCMR. When explants reached the desired stage they were either harvested for RNA, or they were fixed for whole mount in situ hybridization or antibody staining.
Figure 2B:
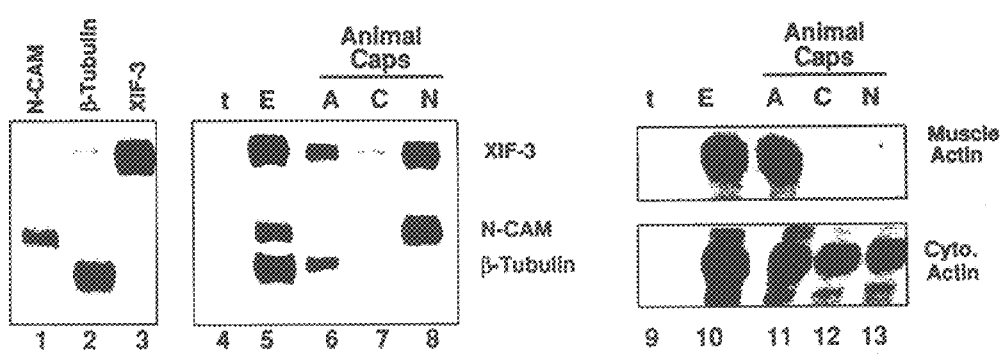
FIG. 2B—Neural induction by noggin in the absence of muscle. Lanes 1–3 show specific fragments protected by N-CAM, β-tubulin, and XIF-3 probes respectively in whole St24 embryo RNA. Lanes 4–8 show protection by the mixture of these three probes while lanes 9–13 show protection by an actin probe on tRNA(t), St24 embryo RNA(E), and RNA collected from St9 AC treated with 50 pM activin (A), 25% of 20 fold concentrated control CHO cell medium (C) or 25% of 20 fold concentrated noggin conditioned CHO cell medium (N). Ubiquitously expressed cytoskeletal actin used as a loading control shows that RNA levels in all treatments are comparable (lanes 11–13).

In order to assess the competence of ectoderm to respond to noggin we treated animal caps taken from blastula (St8), late blastula (St9), early gastrula (St10) and ventral animal caps from mid-gastrula (St10.5) stage embryos with purified human noggin[FIG. 2.]. We also treated similarly staged animal caps with activin to demonstrate its mesoderm inducing and secondary neural inducing activities, and to contrast activin's effects with those of noggin[FIG. 4a.]. Activin treated animal caps show neural induction only in conjunction with induction of dorsal mesoderm, such as muscle and notochord (lanes 3,6,9). In a number of experiments, we confirmed that activin's ability to induce dorsal mesoderm, and consequently neural tissue, declines rapidly at the gastrula stage (lane 12) (Green, et al., Development 108, 173–83, 1990; Kintner and Dodd, Development 113, 1495–1506, 1991). In the experiment shown here a larger than usual dose of activin was given. Under these conditions, only a small amount of neural tissue is made, perhaps because so much mesoderm is induced that there is not much competent ectoderm left in the explant to be neuralized. In contrast noggin can induce neural tissue in animal caps taken from all of these stages without inducing the notochord and somite marker, collagen type II (Amaya, et al., Development 118, 477–87, 1993; Bieker and Yazdani-Buicky, J Histochem Cytochem 40, 1117–20, 1992), or muscle actin (lanes 4,7,10,13). This gives additional support to the proposal that noggin is a direct neural inducer, since it can act in the absence of both early and late mesoderm markers. Furthermore, we have shown that noggin can induce neural tissue in competent ectoderm at a time when mesoderm inducers are inactive.

In some experiments, noggin addition to gastrula (but not blastula) animal caps resulted in induction of muscle (data not shown). This occurred at stages when activin could no longer induce muscle. We interpret this as a result of a dorsalizing action by noggin on tissues that have received a weak mesoderm-inducing signal. The mesoderm-inducing signal which spreads into the gastrula animal cap is not enough to induce mesoderm, but in the presence of Xwnt-8 or noggin, muscle is formed. One interesting corollary of the induction of muscle is that the kinds of neural tissue seen in the explant are modified. Induction in explants that contain no muscle usually yields N-CAM expression, but if muscle is present, expression of both N-CAM and b-tubulin is seen. This phenomenon is demonstrated in the secondary neural induction by activin in St. 9 animal caps[FIG. 2.] and in the comparison of neural tissue induced by noggin in ventral marginal zones versus animal caps [FIG. 6.]. In the ventral marginal zones and animal caps in which muscle is present, both N-CAM and b-tubulin are expressed, whereas induced animal caps without muscle, show only N-CAM expression.

Neural induction after injection of DNA coding for noggin

To confirm our conclusions using a different experimental approach, we have directed noggin expression to gastrula stage animal caps by injecting the plasmid pCSKA-noggin into the animal pole of a one cell stage embryo. This plasmid, in which noggin is under the control of the cytoskeletal actin promoter, turns on the expression of noggin mRNA at the onset of gastrulation (Smith, et al., Nature 361, 547–49, 1993). At the blastula stage, the animal caps are dissected and then matured to tailbud stages for molecular analysis. Animal caps injected with the noggin plasmid show expression of N-CAM in the absence of muscle or notochord markers (FIG. 4c. lane 2). A control plasmid directing the expression of lac Z showed no neural or mesodermal induction as expected (lane 1). This experiment demonstrates that ectopic noggin expression can directly induce neural tissue in gastrula stage ectoderm, a stage when neural induction is taking place in whole embryos.

Differences in competence between dorsal and ventral animal caps.

Figure 5:
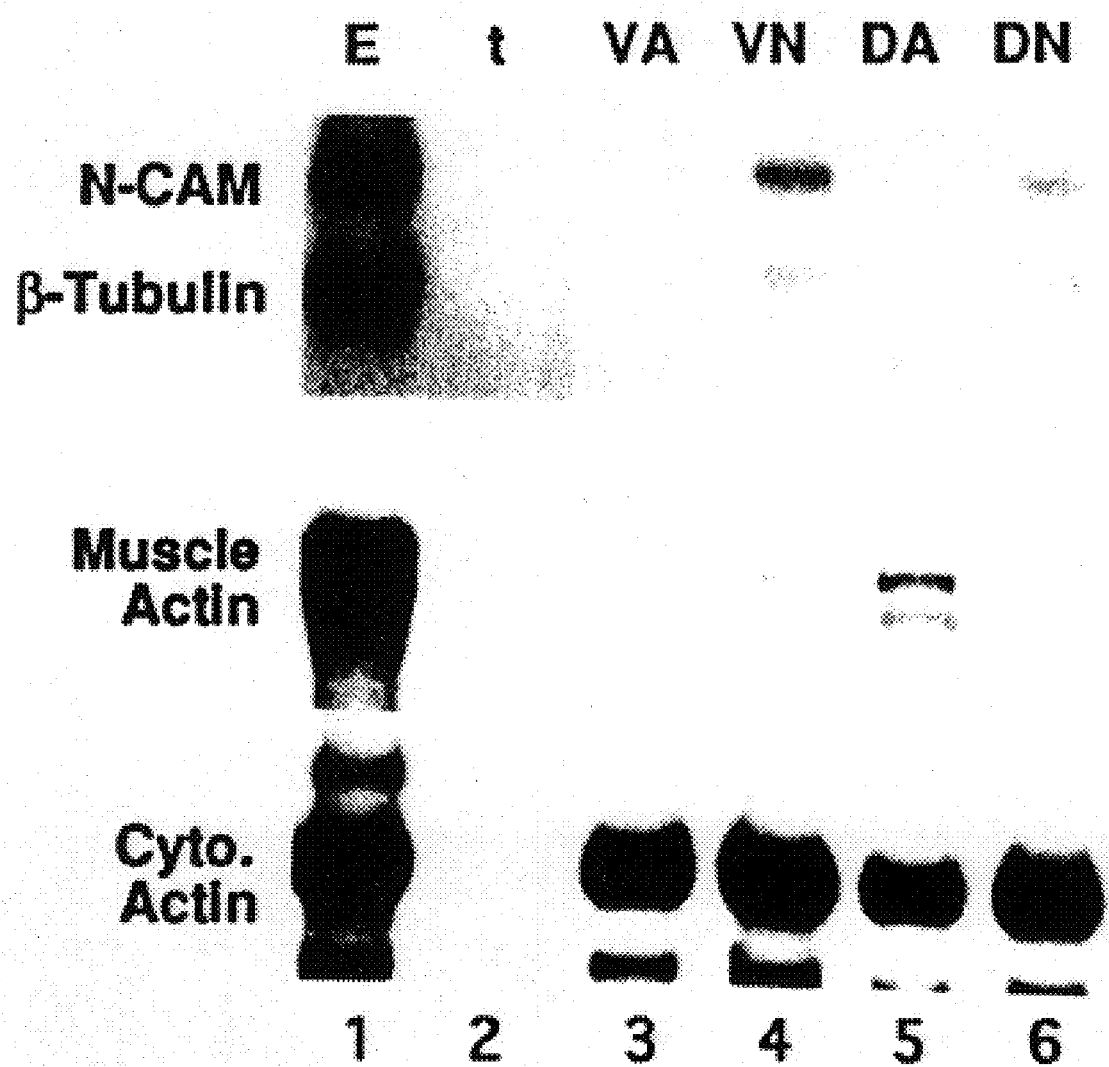
FIG. 5—Responsiveness of dorsal and ventral animal caps to neural induction by noggin. St 105 ventral and dorsal animal caps were dissected as shown in FIGS. 2A–2B. Dorsal and ventral animal caps were treated with activin medium (DA,VA) or 1 μg/ml human noggin (DN, VN) and harvested at St26 for RNase protection analysis using N-CAM, β-tubulin, and actin as probes.

Animal caps taken from the dorsal side of gastrula stage embryos show greater competence to form neural tissue than ventral animal caps (Otte and Moon, Cell 68, 1021–29, 1992; Sharpe, et al., Cell 50, 749–58, 1987), when involuted anterior mesoderm is used as the inducer. This type of mesoderm, however, has weaker inducing capacity than the rest of the involuted mesoderm (Sive, et al., Cell 58, 171–180, 1989). Furthermore, the ventral side of an embryo can support the formation of a complete secondary axis when the organizer is placed on that side (Gimlich and Cooke, Nature 306, 471–3, 1983; Smith and Slack, J. Embryol. Exp. Morph. 78, 299–317, 1983; Spemann, Arch. mikjrosk. Anat. EntwMech. 100, 599–638, 1938), indicating that there is no qualitative difference in competence. Thus, while a weak inducer might unmask slight differences in competence of the ectoderm, it has been suggested that a robust neural inducer would show little difference in its effects on dorsal and ventral ectoderm (Servetnick and Grainger, Development 112, 177–88, 1991). Therefore we tested noggin's effects on dorsal and ventral ectoderm from the early gastrula. No difference in N-CAM expression is detected (FIG. 5, lanes 4,6), while the ventral animal caps treated with noggin show a greater amount of muscle actin expression (presumably through dorsalization of tissues that received a low-grade mesoderm induction). Activin treated dorsal caps show induction of roughly the same level of muscle actin expression (lane 5) as the ventral noggin treated caps, however, activin treatment did not induce detectable neural specific transcripts (lanes 3,5). This indicates that muscle tissue induced at this stage is not sufficient to secondarily induce neural tissue, and that noggin must be present to induce neural tissue.

We conclude that there is no dorsal-ventral difference in noggin mediated neural induction, suggesting that noggin behaves like the robust neural inducing signal of the Spemann organizer, not like the weaker signal from early anterior mesoderm.

Dose Dependence

To determine what levels of noggin protein are required for neural inducing activity, we carried out a dose response experiment. In addition to determining the doses required for neural induction in animal caps, we have also carried out a dose response of the dorsalization of ventral marginal zones in order to compare the doses required for these two types of inductions. Stage 9 animal caps or St. 10.5 VMZ were treated with purified human noggin, and N-CAM and β-tubulin were used to assay neural induction, while muscle actin was used as a marker of dorsal mesoderm. This experiment shows that neural induction occurs at a dose of 1 μg/ml, which is a twenty fold higher dose than required for dorsalization of VMZ [FIG. 5]. There are several observations that may account for the apparently high dose requirement. First, to get a maximal neural response from dorsal mesoderm, the tissues must be left in contact through most of neurulation (Sharpe and Gurdon, Development 109, 765–74, 1990); in contrast, the animal caps treated with noggin close up rapidly, this inhibits factor access, and consequently they receive only a brief effective dose. Second, it is likely that noggin is not the only neural inducer active in the embryo; it has been shown in a variety of amphibians that the somites (Hemmati-Brivanlou, et al., Science 250, 800–802, 1990; Jones and Woodland, Development 107, 785–91, 1989) and the neural plate have neural inducing activity (Hamburger, The Heritage of Experimental Embryology: Hans Spemann and the Organizer, 1988; Servetnick and Grainger, Dev Biol 147, 73–82, 1991) and noggin transcripts are not detected there. Thus it is plausible that noggin is one of several neural-inducing activities. In this connection it is worth noting that noggin is equally potent in inducing neural tissue in ventral marginal zones as in dorsalizing them to generate muscle. Numerous other experiments (see FIG. 5) show that induction of a similar amount of muscle at this stage by activin does not result in neural induction. Fourth, it may be that only a small fraction of the purified protein is active, and that the experiment overestimates the amount of protein needed for neural induction. Finally, it is possible that the accessibility of exogenously added soluble noggin is significantly lower than noggin protein being secreted endogenously.

Patterning

Embryonic neural tissue develops an anteroposterior (A-P) pattern, with various brain structures, eyes, and the spinal cord. It is thought that A-P neural pattern requires the presence of dorsal mesoderm, whether it be adjacent to the responding ectoderm in a planar configuration (Dixon and Kintner, Development 106, 749–757, 1989; Doniach, et al., Science 257, 542–5, 1992; Kintner and Melton, Development 99, 311–25, 1987; Ruiz i Altaba, Development 108, 595–604, 1990), or directly beneath it in a vertical interaction (Dixon and Kintner, Development 106, 749–757, 1989) (Hemmati-Brivanlou, et al., Science 250, 800–802, 1990; Sharpe and Gurdon, Development 109, 765–74, 1990; Sive, et al., Cell 58, 171–180, 1989). Both of these types of interactions occur in normal development, and both probably contribute to the resulting pattern. To determine if noggin induces patterned neural tissue, and if so, what neural regions are represented, we used Xenopus otx as a marker of forebrain and mid brain; En-2 (Hemmati-Brivanlou, et al., Development 111, 715–724, 1991) as a marker of the mid brain-hind brain boundary, and Krox-20 (Wilkinson, et al., Nature 337, 461–4, 1989) as a marker of the third and fifth rhombomeres of the hind brain in in situ hybridization (Harland, Methods in Cell Biology, 36, 675–685, 1991). Antibodies directed against XIHbox 6 (Wright, et al., Development 109, 225–34, 1990) mark posterior hind brain and spinal cord structures. Prior to the use of these markers, we observed the formation of cement glands in noggin treated animal caps. Since cement glands are induced organs of ectodermal origin found anterior to the neural plate, this result suggests that noggin induces anterior structures. In situ hybridization confirms this by showing the presence of a cement gland specific transcript, XAG-1 (Sive, et al., Cell 58, 171–180, 1989) in noggin treated animal caps, but not in control treated animal caps[FIGS. 7A–L.]. In situ hybridization with the region specific neural markers[FIGS. 7A–L.] show that noggin induces forebrain type tissue as seen by the expression of otx in noggin treated animal caps. We have not detected En-2, Krox20, or XIHbox, suggesting that these more posterior markers are not induced by noggin.

Expression of neural antigens

We have demonstrated that noggin directly induces the expression of neural specific transcripts. A further demonstration is to use antibodies against neural specific antigens to show that the noggin induced tissue is phenotypically neural. To this end, we have treated animal cap tissue with noggin and cultured them to a late stage (St 35) for antibody staining. We have used the 6F11 anti-N-CAM antibody, which stains the entire neural tube of a normal embryo. Noggin treated animal caps express this antigen [FIGS. 7A–L.] while control untreated animal caps do not. This indicates that noggin can induce the production of neural specific proteins in treated animal caps. We have failed to detect the expression of numerous other antigens that are characteristic of various subclasses of differentiated neural cells.

These included 2G9, which stains most neural tissue, including peripheral neurons, Tor 24.55, which stains sensory neurons, and Tor 23, which stains a variety of neurons including motor neurons.

Example 7

Production of recombinant human noggin from *E. coli* and baculovirus

Materials and Methods

Genetic Engineering and Cell Culture

A lactose inducible expression plasmid was constructed by replacing the Swa1/Bsm1 region of pRPN40 (Masiakowski et al, J. Neurochem. 57, 1003–1012, 1991) with the Swa1/Bsm1 region of the human noggin gene obtained by PCR and spanned by the same restriction sites, resulting in plasmid pRG301. pRG301 is a high copy number kanamycin resistant plasmid derived from pBR322 with the human noggin gene under the control of the lacUV5 promoter. A plasmid containing the high copy number kanamycin resistant gene was deposited with the Agricultural Research Collection (NRRL), Peoria, Ill., and bears accession number B-18600. This plasmid was described in U.S. patent application Ser. No. 07/478,338, which is incorporated by reference herein in its entirety. *E. coli* W3110laclq cells transformed with pRG301 were grown at 37° C., induced with lactose, harvested by centrifugation, washed once with 100 mM Tris-HCl, 50 mM EDTA pH 8 and stored frozen, essentially as described (Masiakowski et al, ibid.).

Recovery from inclusion bodies

*E. coli* cell paste (32 g) was suspended in ten volumes (v/w) of 50 mM TrisHCl-pH 8.0–5 mM EDTA, lysed in a French Press at 8,000 psi and 8° C. and centrifuged at 8,000× g for 30 min at 4° C. The pellet containing noggin was suspended in the original volume of 2 M urea-20 mM TrisHCl, pH 8.0 and stirred for 30 min. The suspension was centrifuged at 8,000× g at 4° C. for 30 min and the pellet consisting mostly of inclusion bodies (IB) was suspended in 20 volumes (v/w) of 6 M guanidine HCl, 50 mM TrisHCl,1 mM EDTA, 50 mM DTT and stirred for one hour at room temperature. After centrifugation at 8,000× g for 30 min, the supernatant containing 0.45–0.50 g denatured and reduced noggin was diafiltered against 10 volumes of 6 M urea-50 mM sodium acetate pH 4.5–1 mM EDTA-0.1 mM DTT using Omega 10,000 MW cut-off membranes. The diafiltrate containing 0.4–0.44 g noggin was loaded at a flow rate of 30 ml/min onto a 2.6×10 cm column of S-Sepharose (Pharmacia), equilibrated in 6 M urea-50 mM sodium acetate-1 mM EDTA-0.1 mM DTT pH 4.5. The column was first washed with the same buffer and then with a one liter gradient (0–1M NaCl) at a flow rate of 30 ml/min. Fractions containing noggin were identified by gel electrophoresis and pooled. The yield was 0.2–0.25 g noggin.

Refolding.

Figure 8:
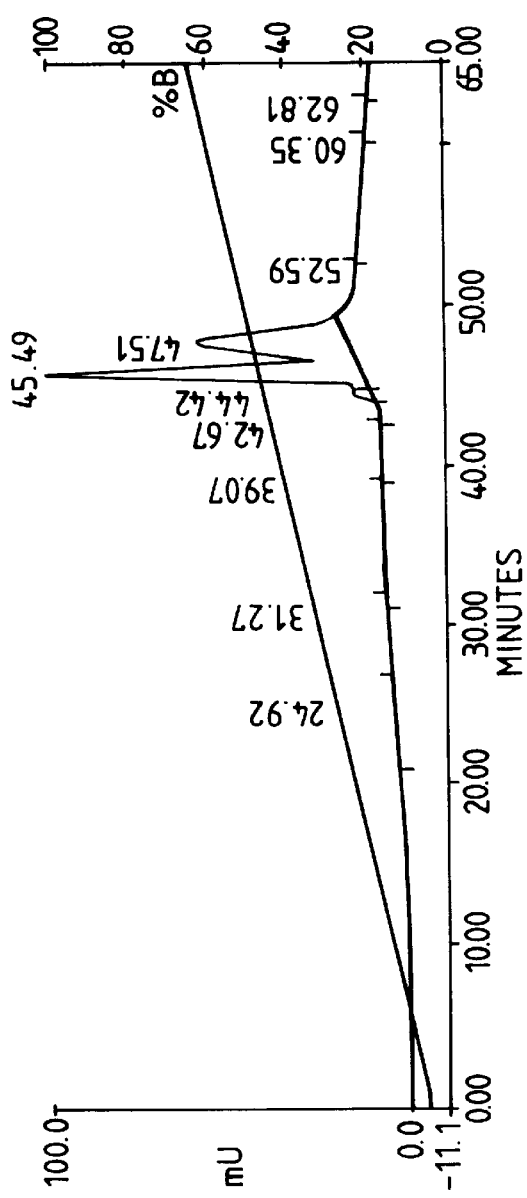
FIG. 8—Reverse phase HPLC profile of two refolded isoforms of noggin. The refolded noggin solution was applied onto a Brownlee Aquapore AX-300, 0.46×22 cmH-PLC column at a flow rate of 1 ml/min. The column was equilibrated with solvent A containing 0.1% TFA in water. Solvent B was 0.1% TRA in acetonitrile. The column was developed according to the following protocol: a) 2 min isocratically at 95% of solvent A-5% of solvent B; 60 min linear gradient to 65% of solvent B and 35% of solvent A. Correctly refolded noggin elutes earlier at 44%–46% solvent B.

The denatured and reduced noggin solution was adjusted to 0.05–0.2 mg/ml protein concentration and brought to 1.5–2.5 M guanidineHCl-0.1 M TrisHCl pH 8.0–0.1 mM EDTA-0.2–2 mM reduced glutathione-0.02–0.2 mM oxidized glutathione (preferably at a ratio of 10:1 reduced to oxidized glutathione) at 4° C. under slow stirring. After 24–72 hours, two refolded noggin isoforms were identified by RP-HPLC chromatography (FIG. 8). The refolded noggin solution was diafiltered against 20 volumes of 0.05 M sodium acetate pH 4.5, brought to 50 mM potassium phosphate pH 7.2 and stirred slowly at 4° C. for 1 hour minimum. Misfolded noggin precipitated and was removed by centrifugation for 30 min at 8,000× g.

Reverse phase HPLC chromatography.

Refolded noggin can be purified by chromatography on a 12 mm C8, 1×25 cm Dynamax 300 A column equilibrated in solvent A (0.1% TFA in water). After loading, the column was washed with solvent A and was developed at a flow rate of 4 ml/min according to the following protocol: (a) 10 min isocratically at 70% of solvent A, 30% of solvent B (0.1% TFA in acetonitrile); 30 min linear gradient to 60% solvent B and 40% solvent A. Correctly refolded noggin elutes earlier at 44%–46% solvent B. The yield was 0.07–0.1 g noggin.

Production of human noggin in Baculovirus cell culture.

The SF21 line of Spodoptera frugiperda was routinely maintained as cell monolayers in Grace's Insect Cell medium supplemented with lactalbumin hydrolysate and yeastolate (Gibco). This medium completed with 10% v/v heat-inactivated fetal calf serum (Irvine Scientific) is identified as TMNFH-10. Cells were also cultured in serum-free medium (SF-900-11; Gibco) after adaptation. Suspension cultures in either medium were raised in microcarrier culture flasks (Bellco) using a stirring speed of 80 rpm. All cultures were maintained at >96% viability, as judged by trypan blue exclusion.

Construction of recombinant baculovirus.

Sequences corresponding to human noggin were excised as a 5'-BamH1-Pst1-3' fragment from an expression plasmid containing the human noggin gene. This fragment was inserted into BamH1-Pst1 digested pVL1393 (Invitrogen). The resulting plasmid, pTR 1009, has the human noggin sequence immediately downstream of the polyhedrin promoter of Autographa californica Multiple Nuclear Polyhedrosis Virus (AcMNPV), and this promoter-heterologous gene fusion is flanked in turn by recombination targets derived from the AcMNPV polyhedrin region. Recombinant plasmid DNA was purified by alkaline lysis and CsCl centrifugation. SF21 cells were co-transfected with plasmid and viral DNA by the following method: Plasmid DNA (3 mg) was mixed with 0.5 mg linearized, deleted viral DNA (Baculo Gold™, Pharminigen), and precipitated with ethanol. Dried DNA was then resuspended in water (50 ml), mixed with 1.5 ml Grace's medium, and 30 ml Lipofectin™ cationic liposomes (BRL). The DNA-liposome mixture was vortexed, allowed to stand at room temperature for 15 minutes and added dropwise to a monolayer of SF21 cells (2×106 cells/60 mm plate). After incubation at 27° C. for four hours, 2 ml TMNFH-10 was added and the culture returned to incubation for 5 days. Tissue culture medium was harvested and used as a source of virus for plaque isolation. Recombinant virus was isolated by multiple rounds of plaque purification on SF21 cells. Diluted virus (0.5 ml) was adsorbed to cell monolayers (2×106 cells/60 mm plate) for a period of one hour at 27° C., aspirated, and virus plaques were allowed to develop with an overlay of 0.5% agarose in TMNFH-10 medium for a period of 6 days. Virus plaques were picked after microscopic inspection, and eluted into 2 ml SF900-II medium. Virus stocks were amplified by low multiplicity (0.1 pfu/cell) infection. Virus clones expressing noggin were identified by metabolic labeling of infected cultures with 35S-methionine and 35S-cysteine and analysing total labeled protein by polyacrylamide gel electrophoresis and autoradiography. A labeled protein of the expected apparent Mr of 20,000–30,000 was detected by this method in candidate clones but not in control cultures.

Expression and purification of baculovirus-derived noggin.

SF21 cells were cultured in suspension flasks to a density of approximately 1.8×106/ml in SF900-II medium. Cultures (500 ml) were collected by centrifugation at 1000× g for 10 min and resuspended in 20 ml of growth medium containing 5–10 pfu/cell recombinant virus. Virus was allowed to adsorb for 1 hour at room temperature with gentle mixing. Infected cells were then diluted to their original volume with fresh growth medium, and incubated at 27° C. for 3 days. Cells and debris were subsequently clarified from the growth medium by centrifugation at 1000× g for 20 min.

Cell supernatants were brought to pH 8.0, passed through a 0.45 mm Millipak 60 filter and applied to a Fast S column that had been equilibrated in 25 mM HEPES pH 8.0. The column was washed with the same buffer and developed with a linear NaCl gradient to remove other medium components. Noggin eluted from this column at 1 M NaCl.

Results

Characterization of human noggin produced in *E. coli* and in baculovirus

Figure 9:
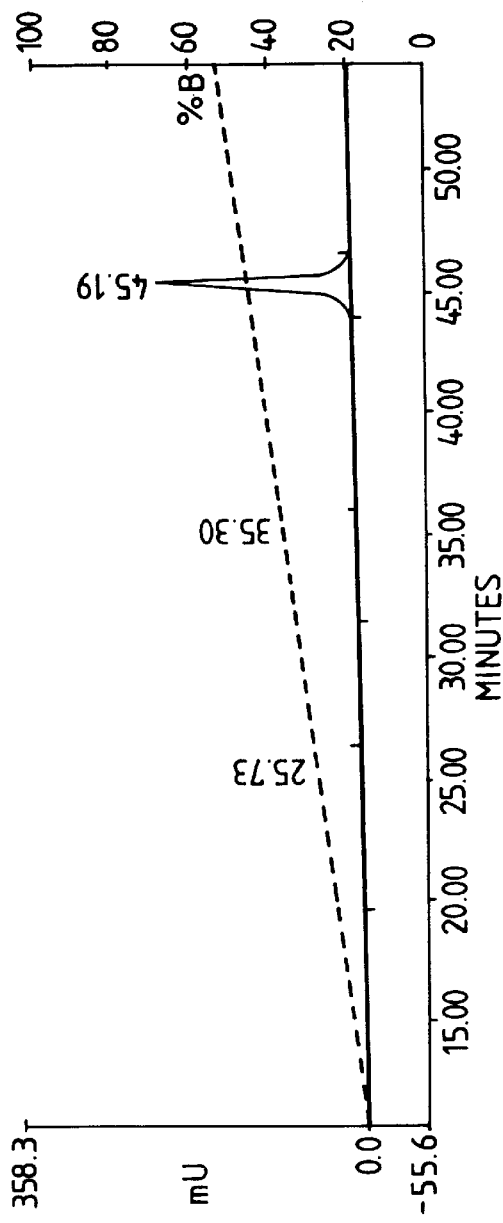
FIG. 9—Reverse-phase HPLC chromatography characterization of recombinant noggin refolded and purified from E. Coli Conditions as in the legend to FIG. 8.

Reverse-phase HPLC chromatography shows that recombinant noggin refolded and purified from *E. coli* elutes in a single sharp peak, indicating the presence of one predominant isoform (FIG. 9).

Electrophoresis on 15% polyacrylamide-SDS-reducing gels shows that noggin from either *E. coli* or insect cells is better than 95% pure and migrates in a single band corresponding to a protein of 20–30 kD. Noggin from insect cells shows slightly slower mobility, apparently due to additional mass from N-linked glycosylation at the single consensus site (FIG. 10). Treatment with Endo F converts the mobility of insect-produced noggin to that of the bacterially produced protein (data not shown).

In the absence of reducing agents, noggin produced either in *E.coli* or in baculovirus behaves as a disulfide-linked oligomeric protein (FIG. 10). However, by gel filtration analysis and mass spectroscopy noggin is primarily a dimeric protein (data not shown).

Figure 11:
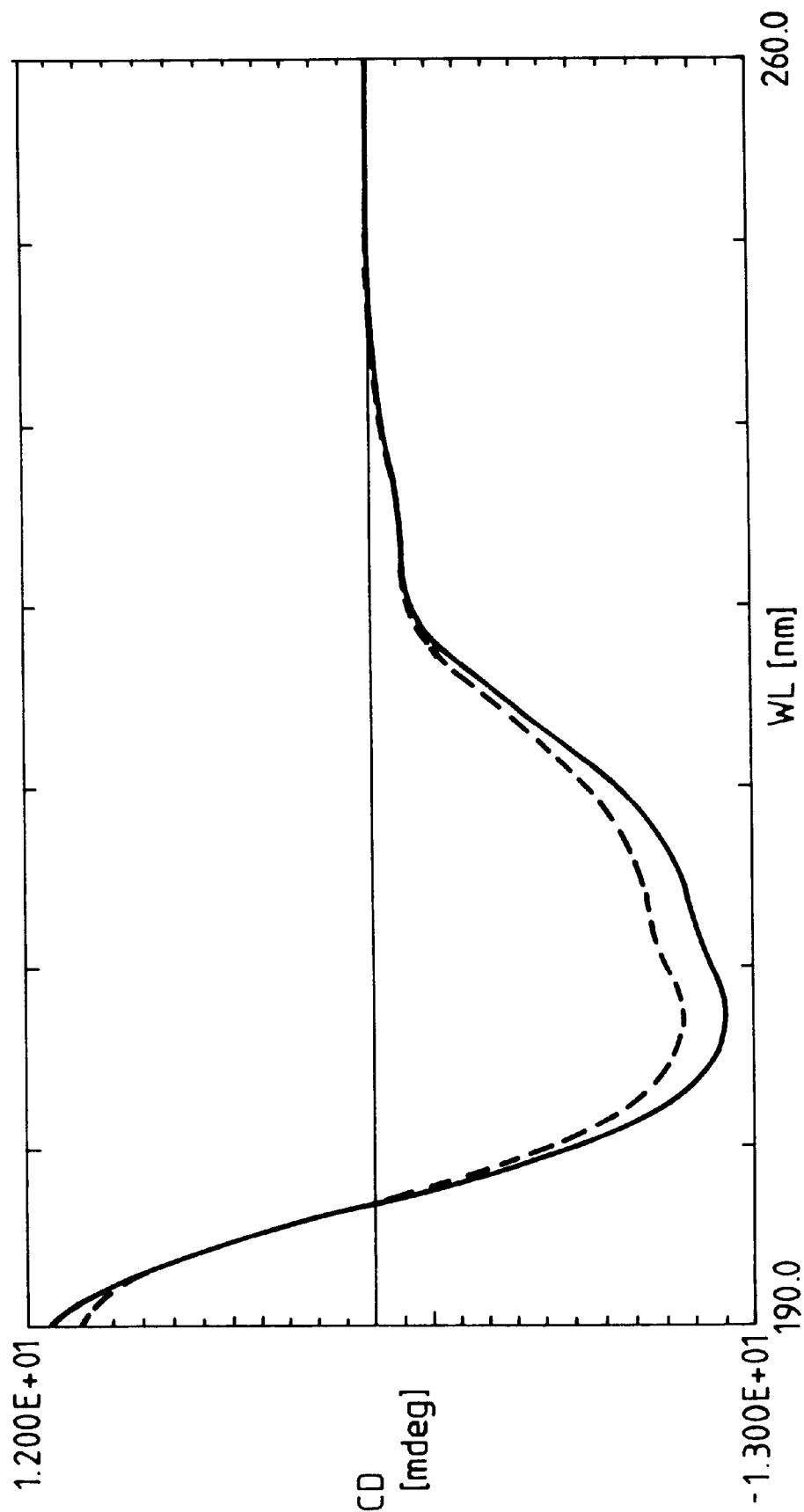
FIG. 11—Circular dichroism spectra of recombinant noggin produced in E. coli (--), and in insect cells (-).

Circular dichroism studies show that recombinant noggin refolded and purified from *E. coli* as well as noggin purified from insect cells have very similar conformations (FIG. 11). Secondary structure determined by this method indicates that noggin consists of 48% alpha-helix, 0% beta-structure, and 52% random coil.

Biological Activity of human noggin produced in *E. coli* and in baculovirus

Biological activity of human noggin produced in *E. coli* or in baculovirus was determined by assay of muscle actin expression in the ventral marginal zone assay, as described supra. Results shown in FIG. 12 indicate a positive dose response for induction of muscle actin mRNA in VMZ exposed to either bacterially produced human noggin, or baculovirus produced human noggin.

Example 8

Production and characterization of rat monoclonal antibody RP57-16 reactive with human noggin.

Materials and Methods

Production of antibody

RP57-16 rat monoclonal antibody reactive with recombinant human and Xenopus noggin was produced by the immunization of a female Lewis rat with four 35 µg injections of purified recombinant human noggin (produced in *E. coli*) over a two month period. For the initial immunization, the protein was injected in the rear foot pad in Freund's complete adjuvant. Subsequent injections were given in the same foot pad in Freund's incomplete adjuvant. The rat was euthanized 3 days after the fourth injection.

Lymph node cells from the immunized rat were mixed with SP2/0-E.O. mouse myeloma cells at a ratio of 2:1. After centrifugation, the cell mixture was resuspended in 0.25 ml of 42% (w/v) PEG 3350 (Baker) in phosphate-buffer-saline with 10% (v/v) dimethylsulfoxide (Sigma) for a total of 3 minutes in a 37° C. water bath. Cells were plated at a density of $5 \times 10^4$ lymphocytes per well in 96-well plates (Falcon 3072) in DMEM/F-12 (Mediatech, Inc.) containing 10% FBS (supplemented with streptomycin, penicillin, pyruvate, and glutamine) and HMGT (1.6×10-3 M thymidine, 4.0× 10-4 methotrexate, 1.3×10-3 sodium bicarbonate and 1.0× 10-2 hypoxanthine). After 10 days in culture, supernatants were harvested and assayed for antibody activity against recombinant human noggin by indirect ELISA. Supernatant from COS-M5 cells transfected with the plasmid containing the human noggin gene was air dried overnight in Probind 96-well assay plates (Falcon 3915). Non-specific binding was eliminated by 2 hour incubation at ambient temperature with PBS/1% BSA (Sigma). Plates were washed 2 times with PBS/0.02% Tween 20. Culture supernants were then added and incubated at ambient temperature for 1 hour. Plates were washed 4 times with PBS/0.02% Tween 20. Secondary antibody, Goat anti-Rat IgG (H+L) alkaline phosphatase conjugate(Caltag) diluted 1:2000 in PBS/1% BSA was added to each well and the plates incubated at ambient temperature for 1 hour. Plates were again washed 4 times with PBS/0.02% Tween 20. Antibody binding was visualized by 1 hour incubation at ambient temperature in the dark with pNPP (p-nitrophenyl phosphate, Sigma) 1 mg/ml in diethanolamine buffer, pH 9.8. The reaction was stopped by the addition of an equal volume of 100 mM EDTA. Absorbance was read at 405 nm on a Thermomax Microplate Reader (Molecular Devices). A reaction was considered positive if the absorbance was 2 times that of the negative control (diluent alone followed by secondary antibody and substrate). Positive clones were expanded and culture supernatant containing monoclonal antibody was collected for specificity analysis.

RP57-16 was cloned in soft agar. Cloned hybrid cells were expanded in DMEM/F-12 (Mediatech, Inc.) containing 10% FBS (supplemented with streptomycin, penicillin, pyruvate, and glutamine).

Supernatant containing antibody was aliquoted and stored at −70° C. until use.

Specificity Analysis

Elisa 100 ng of purified recombinant human noggin, Xenopus noggin, BDNF, NT-3, and NT4 protein was individually passively adsorbed to Probind 96-well assay plates by overnight incubation at 4° C. in 50 mM bicarbonate buffer, pH 9.6. BDNF, NT-3 and NT-4 were used to assess non-specific binding of rat monoclonal antibody RP57-16.

Supernatants from COS-M5 cells transfected with either the plasmid containing the human noggin gene or the plasmid containing the fig C-terminal tagged Xenopus noggin gene were air dried to Probind 96-well plates overnight. Non-specific binding was eliminated by 2 hour incubation at ambient temperature with PBS/1% BSA (Sigma). Plates were washed 2 times with PBS/0.02% Tween 20. Undiluted RP57-16 was added and incubated at ambient temperature for 1 hour. Plates were washed 4 times with PBS/0.02% Tween 20. Secondary antibody, Goat anti-Rat IgG (H+L) alkaline phosphatase conjugate(Caltag) diluted 1:2000 in PBS/1% BSA was added to each well and the plates incubated at ambient temperature for 1 hour. Plates were again washed 4 times with PBS/0.02% Tween 20. Antibody binding was visualized by 1 hour incubation at ambient temperature in the dark with pNPP (p-nitrophenyl phosphate, Sigma) 1 mg/ml in diethanolamine buffer, pH 9.8. The reaction was stopped by the addition of an equal volume of 100 mM EDTA. Absorbance was read at 405 nm on a Thermomax Microplate Reader (Molecular Devices). A reaction was considered positive if the absorbance was 2 times that of the negative control (diluent alone followed by secondary antibody and substrate).

Electrophoresis and Western Blotting

Rat monoclonal antibody RP57-16 was also analyzed by Western blotting. 50 ng of recombinant human noggin, non-reduced and reduced, were electrophoresed on 12.5% SDS-polyacrylamide gels and electroblotted on nitrocellulose membranes. Membranes were blocked with PBS/1% Casein/0.1% Tween 20, and then incubated for 2 hours with undiluted RP57-16 culture supernatant. Following 4 washes in PBS/0.02% Tween 20, the membranes were incubated with a 1:5000 dilution of Goat anti-Rat IgG (H+L) horseradish peroxidase conjugate (Pelfreeze) in PBS/1% BSA/ 0.1% Tween 20. Membranes were washed 4 times with PBS/0.02% Tween 20. Proteins were visualized with ECL Western Blotting Reagents (Amersham) according to the manufacturer's instructions. Membranes were then exposed to XAR 5 Scientific Imaging film (Kodak) for 5 seconds.

Results

Rat monoclonal antibody RP57-16 reacts with both recombinant human and Xenopus noggin and with recombinant human noggin produced in *E. coli*, in insect cells, and in COS-M5 cells. The antibody does not react with the neurotrophins BDNF, NT-3 and NT-4. Western blotting showed that the antibody detects both reduced and non-reduced protein.

Example 9

Creation of Noggin Deletion Muteins

The subject invention further concerns the discovery that native human noggin can be modified to create new compounds with highly desirable characteristics.

The basic region of Xenopus noggin corresponds to amino acids 123–135 (KKHRLSKKLRRKL) (corresponding to residues 133–145 of SEQ ID NO: 2 wherein Q at position 135 is substituted with H) of the molecule. (See Smith, W. C. and Harland, R. M. Cell 70: 829–840 (1992) for sequence). Based upon what was known about the TGF-β family of molecules, the basic region appeared to be a possible processing site. To better understand the function of the basic region, constructs of Xenopus noggin were created that deleted the highly conserved basic region (Δ123–135) or a larger portion of the peptide including the basic region (Δ91–135). Both of these deletion mutants were active, yielding hyperdorsalized embryos when injected as RNA. In addition, preliminary experiments demonstrated that noggin had an affinity for heparin, while a modified form with the basic region deleted did not possess this binding activity.

Native human noggin (hNG) exhibits low bioavailability in animal sera, likely due to its binding to extracellular matrix. Fc-tagged human noggin (hNG-Fc) has been shown to bind to BMP4 with very high affinity. (Zimmerman, L. B., et al., Cell 86: 599–606 (1996)). Modification of hNG has resulted in the identification of compounds which show improved bioavailability while retaining the ability to bind and antagonize Bone Morphogenetic Proteins (BMPs). The specific modifications resulting in altered biological properties involve deletion of amino acids identified as responsible for conferring heparin binding activity to the native noggin molecule. The resulting modified noggin lacks heparin binding activity but, unexpectedly, retains the ability to bind and antagonize BMP4.

Specifically, applicants have created two molecules, known as hNGΔ138–144Fc and hNGΔ133–144Fc. These molecules are Fc-tagged deletion muteins of human noggin lacking either amino acids 138 to 144 (for hNGΔ138–144Fc) or 133 to 144 (for hNGΔ133–144Fc) and tagged with the Fc domain of human IgG1 at their C-termini. To construct Fc-tagged noggins, a BspEI-NotI human IgG1 fragment (See Davis, S., et al., Science 266: 816–819 (1994); Economides, A. N., et al., Science 270: 1351–1353 (1995)) may be fused to human noggin using an oligonucleotide encoding a peptide bridge sequence as described by Zimmerman, L. B., et al., Cell 86: 599–606 (1996). As described below, the deletion muteins hNGΔ138–144Fc and hNGΔ133–144Fc displayed identical activity with hNG-Fc for binding to BMP4, as well as reduced affinity for heparin and superior pharmacokinetics in animal sera as compared to hNG.

Construction of hNGΔ133–144Fc hNGΔ133–144Fc consists of the sequence of human noggin (hNG) with a deletion of amino acids 133 to 144 (numbering begins with the initiating methionine being amino acid number 1), fused to the constant region of human immunoglobulin G1 (Fc) via a Ser-Gly "bridge" (encoded by a genetically engineered Bsp EI restriction enzyme site) (FIG. 14) SEQ ID NO: 23. hNGΔ133–144Fc was constructed by PCR and was cloned into the mammalian expression vector pMT21 (pMT21.hNGΔ133–144Fc) using standard genetic engineering techniques. The correctness of the sequence of hNGΔ133–144Fc was verified by sequencing. Subsequently, this deletion mutein was also transferred to the expression vector psRa, and both the Fc-tagged and the untagged version of this hNG mutein were constructed (psRa.hNGΔ133–144Fc, and psRa.hNGΔ133–144 respectively).

Expression of hNGΔ133–144Fc hNGΔ133–144Fc was initially expressed in COS7 cells using a Lipofectamine (GIBCO/BRL) based transfection protocol. hNGΔ133–144Fc, which like hNG is secreted, was purified from the conditioned media by passing through a Protein A-Sepharose column (Pharmacia) and eluting it with 100 mM acetic acid which was subsequently neutralized with Tris buffer to pH 7. The purity of this preparation was checked by SDS-PAGE followed by staining with the fluorescent dye SYPRO Orange (Molecular Probes, Inc.). The resulting preparation was more than 90% pure by this criteria and it was primarily in a disulfide-linked dimeric form, in agreement with previous observations made both with untagged hNG as well as with hNG-Fc, both of which also form disulfide-linked dimers.

Activity of hNGΔ133–144Fc

Figure 15:
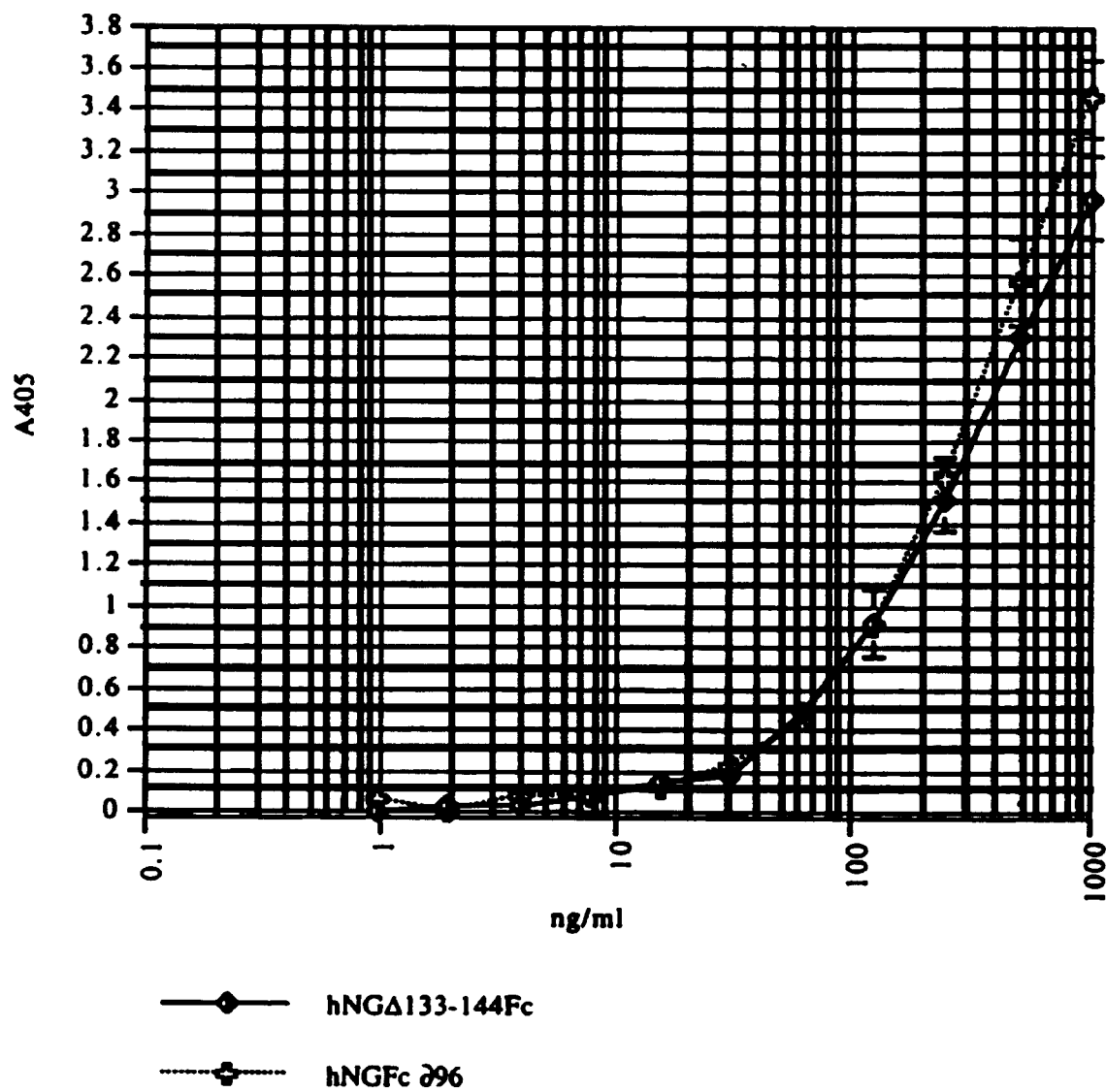
FIG. 15—hNGΔ133–144Fc binds to human BMP4
The activity of either hNG or hNGΔ133–144Fc was tested by comparing their ability to bind to human Bone Morphogenetic Protein 4 (hBMP4). hBMP4 (2 μg/ml) was coated on ELISA plates (CORNING) by passive binding. Unbound hBMP4 was removed by washing four times with PBS, and the plates were blocked with 1% BSA in PBS. A standard curve of hNG-Fc was performed to show dose-depended binding of hNG-Fc to hBMP4 and compared to identical amounts of hNGΔ133–144Fc. After a 1 hour incubation unbound hNG-Fc or hNGΔ133–144Fc was removed by washing four times with PBS, and 0.5 μg/ml anti-human IgG·Alkaline Phosphatase conjugate (anti-Fc·AP) was added to each well. After a 1 hour incubation unbound anti-Fc·AP was removed by washing four times with TBS+ 0.1% Tween and then Alkaline Phosphatase substrate (para-nitrophenyl phosphate; Sigma) was added. Alkaline Phosphatase converts this substrate to a product whose production can be monitored by measuring Absorbance at 405 nm. The ability of hNG or hNGΔ133–144Fc to bind to BMP4 was visualized by comparing A405 units.
Note: There is no binding of hNG-Fc or hNGΔ133–144Fc to the plates if hBMP4 is omitted.

Binding to BMP4:

To determine if this hNG mutein was active, its ability to bind to hBMP4 was compared with that of hNG-Fc, which binds human Bone Morphogenetic Protein 4 (hBMP4) with affinity essentially identical to that of untagged hNG. An ELISA format assay where hBMP4 is captured on the surface of an ELISA plate was used to compare the two proteins. The hNGΔ133–144Fc mutein displayed the same binding to BMP4 as hNG-Fc (FIG. 15), indicating that the two proteins have the same biological activity.

Binding to Heparin:

We examined the heparin binding profile of hNG-Fc and compared it with that of hNGΔ133–144Fc and another hNG deletion mutein which bears a shorter deletion in the basic region, namely, hNGΔ138–144Fc (also referred to as hNGΔKKLRRK-Fc). As shown on FIG. 16, hNG-Fc starts to elute from heparin at about 0.75 M NaCl, whereas hNGΔ133–144Fc and hNGΔ138–144Fc start eluting at 0.25 M NaCl. Binding to heparin at above 0.5 M NaCl is considered to be an affinity interaction with heparin whereas binding to heparin below 0.5 M NaCl is considered to be due to ionic interactions (heparin contains sulfate groups which are negatively charged and hNG has regions which are positively charged). Therefore, it appears that the two hNG deletion muteins, hNGΔ133–144Fc and hNGΔ138–144Fc interact with heparin through ionic interactions whereas hNG-Fc displays an affinity for heparin. Since the KKLRRK (residues 139–144 of SEQ ID NO: 2) deletion (i.e. that embodied by hNGΔ138–144Fc) is adequate for reducing the interaction with heparin to that expected for ionic effects, we conclude that the sequence KKLRRK (residues 139–144 of SEQ ID NO: 2) (i.e. amino acids 138 to 144 in hNG) is or contains the heparin binding domain of hNG. The Fc-domain did not bind to heparin.

We have also found that hNG and hNG-Fc display identical binding to heparin by the method described above, whereas a chemically modified form of hNG (citraconyl-hNG) does not bind to heparin. We have also examined the heparin binding profile of another hNG deletion mutein that bears a longer deletion beyond the basic region, namely hNGΔ133– 179Fc. hNGΔ133–179Fc displays the same binding profile to heparin as hNGΔ133–144Fc and hNGΔ138–144Fc, indicating that further deletion of the sequence downstream of the basic region does not further reduce the ionic component of hNG binding to heparin. From this we conclude that the ionic component of hNG binding to heparin must reside within the Kunitz-like domain of hNG. Furthermore, the chemically modified citraconyl-hNG and the two deletion muteins hNGΔ138–144Fc and hNGΔ133–144Fc are all biologically active (i.e. they bind to BMP4 with the same apparent affinity as hNG-Fc), whereas the deletion mutein hNGΔ133–179Fc is inactive. Taken together, these results indicate that binding of hNG to heparin can be separated from binding to BMP4, and that the heparin binding domain of hNG is not required for its BMP4 blocking activity.

Pharmacokinetic profile of hNGΔ133–144Fc

The pharmacokinetic properties of hNGΔ133–144Fc were tested in both mice and rats. It had been previously determined that unmodified hNG expressed in *E. coli* and refolded displays very poor bioavailability in rat serum after intravenous administration, with an apparent half life of less than 60 minutes. Citraconyl-hNG, which does not bind to heparin, displays a 30-fold improvement in bioavailability but also disappears from circulation at about 2 hours post-injection. We reasoned that hNGΔ133–144Fc which does not bind to heparin and which also has an Fc-tag may have a longer half-life in vivo. To examine this possibility, we injected mice and rats with hNGΔ133–144Fc and determined its bioavailability in sera.

When hNGΔ133–144Fc was injected into mice intraperitoneously (ip), it was detectable even in the latest time point sampled, which was 24 hours, achieving levels of 2 μg/ml (FIG. 17A). Intravenous injection in rat also showed favorable pharmacokinetics, although the latest serum sample was taken at 6 hours. In that experiment approximately 18 μg/ml of hNGΔ133–144Fc were detected (FIG. 17B). Similar results have been achieved with hNGΔ138–144Fc, indicating that deletion of the heparin binding domain of hNG is responsible for the improved pharmacokinetic profile of these molecules over hNG. Since the assay used to detect hNGΔ133–144Fc post-ip or post-iv injection in animal sera relies on the ability of hNGΔ133–144Fc to bind to BMP4, we also know that the hNGΔ133–144Fc that is detected is functional and capable of interacting with BMP4. Furthermore, since hNG displays a very high affinity for BMP4, we anticipate that the levels of hNGΔ133–144Fc achieved in these experiments will block BMP4 activity in animal model and in clinical situations.

Deposit of Microorganisms

The following were deposited with the American Type Culture Collection, 12301 Parklawn Drive, Rockville, Md. 20852 under the terms of the Budapest Treaty:

|  |  | ATCC No. | Date of Deposit |
|---|---|---|---|
| phage | hnogλ-5 | 75311 | 9-23-92 |
| phage | hnogλ-7 | 75309 | 9-23-92 |
| phage | hnogλ-9 | 75310 | 9-23-92 |
| phage | hnogλ-10 | 75308 | 9-23-92 |
| hybridoma | RP57-16 | CRL 11446 | 8-25-93 |

While the invention has been described above in conjunction with preferred specific embodiments, the description and examples are intended to illustrate, and not to limit, the scope of the invention.

SEQUENCE LISTING

<160> NUMBER OF SEQ ID NOS: 23

<210> SEQ ID NO 1
<211> LENGTH: 699
<212> TYPE: DNA
<213> ORGANISM: human
<220> FEATURE:
<221> NAME/KEY: CDS
<222> LOCATION: (1)..(696)

<400> SEQUENCE: 1

```
atg gag cgc tgc ccc agc cta ggg gtc acc ctc tac gcc ctg gtg gtg      48
Met Glu Arg Cys Pro Ser Leu Gly Val Thr Leu Tyr Ala Leu Val Val
  1               5                  10                  15 gtc ctg ggg ctg cgg gcg aca ccg gcc ggc ggc cag cac tat ctc cac      96
Val Leu Gly Leu Arg Ala Thr Pro Ala Gly Gly Gln His Tyr Leu His
             20                  25                  30 atc cgc ccg gca ccc agc gac aac ctg ccc ctg gtg gac ctc atc gaa     144
Ile Arg Pro Ala Pro Ser Asp Asn Leu Pro Leu Val Asp Leu Ile Glu
         35                  40                  45 cac cca gac cct atc ttt gac ccc aag gaa aag gat ctg aac gag acg     192
His Pro Asp Pro Ile Phe Asp Pro Lys Glu Lys Asp Leu Asn Glu Thr
     50                  55                  60 ctg ctg cgc tcg ctg ctc ggg ggc cac tac gac cca ggc ttc atg gcc     240
Leu Leu Arg Ser Leu Leu Gly Gly His Tyr Asp Pro Gly Phe Met Ala
 65                  70                  75                  80 acc tcg ccc ccc gag gac cgg ccc ggc ggg ggc ggt gca gct ggg          288
Thr Ser Pro Pro Glu Asp Arg Pro Gly Gly Gly Gly Ala Ala Gly
                 85                  90                  95 ggc gcg gag gac ctg gcg gag ctg gac cag ctg ctg cgg cag cgg ccg     336
Gly Ala Glu Asp Leu Ala Glu Leu Asp Gln Leu Leu Arg Gln Arg Pro
            100                 105                 110 tcg ggg gcc atg ccg agc gag atc aaa ggg cta gag ttc tcc gag ggc     384
```

-continued

```
ser gly ala met pro ser glu ile lys gly leu glu phe ser glu gly
Ser Gly Ala Met Pro Ser Glu Ile Lys Gly Leu Glu Phe Ser Glu Gly
        115                 120                 125 ttg gcc cag ggc aag aag cag cgc cta agc aag aag ctg cgg agg aag    432
Leu Ala Gln Gly Lys Lys Gln Arg Leu Ser Lys Lys Leu Arg Arg Lys
130                 135                 140 tta cag atg tgg ctg tgg tcg cag aca ttc tgc ccc gtg ctg tac gcg    480
Leu Gln Met Trp Leu Trp Ser Gln Thr Phe Cys Pro Val Leu Tyr Ala
145                 150                 155                 160 tgg aac gac ctg ggc agc cgc ttt tgg ccg cgc tac gtg aag gtg ggc    528
Trp Asn Asp Leu Gly Ser Arg Phe Trp Pro Arg Tyr Val Lys Val Gly
                165                 170                 175 agc tgc ttc agt aag cgc tcg tgc tcc gtg ccc gag ggc atg gtg tgc    576
Ser Cys Phe Ser Lys Arg Ser Cys Ser Val Pro Glu Gly Met Val Cys
        180                 185                 190 aag ccg tcc aag tcc gtg cac ctc acg gtg ctg cgg tgg cgc tgt cag    624
Lys Pro Ser Lys Ser Val His Leu Thr Val Leu Arg Trp Arg Cys Gln
            195                 200                 205 cgg cgc ggg ggc cag cgc tgc ggc tgg att ccc atc cag tac ccc atc    672
Arg Arg Gly Gly Gln Arg Cys Gly Trp Ile Pro Ile Gln Tyr Pro Ile
        210                 215                 220 att tcc gag tgc aag tgc tcg tgc tag                                699
Ile Ser Glu Cys Lys Cys Ser Cys
        225                 230

<210> SEQ ID NO 2
<211> LENGTH: 232
<212> TYPE: PRT
<213> ORGANISM: human

<400> SEQUENCE: 2

Met Glu Arg Cys Pro Ser Leu Gly Val Thr Leu Tyr Ala Leu Val Val
  1               5                  10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
        115                 120                 125

Leu Ala Gln Gly Lys Lys Gln Arg Leu Ser Lys Lys Leu Arg Arg Lys
    130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
        195                 200                 205

Arg Arg Gly Gly Gln Arg Cys Gly Trp Ile Pro Ile Gln Tyr Pro Ile
```

-continued

```
                210                 215                 220

Ile Ser Glu Cys Lys Cys Ser Cys
225                 230

<210> SEQ ID NO 3
<211> LENGTH: 14
<212> TYPE: PRT
<213> ORGANISM: frog and mouse

<400> SEQUENCE: 3

Gln Met Trp Leu Trp Ser Gln Thr Phe Cys Pro Val Leu Tyr
1               5                   10

<210> SEQ ID NO 4
<211> LENGTH: 12
<212> TYPE: PRT
<213> ORGANISM: frog and mouse

<400> SEQUENCE: 4

Arg Phe Trp Pro Arg Tyr Val Lys Val Gly Ser Cys
1               5                   10

<210> SEQ ID NO 5
<211> LENGTH: 14
<212> TYPE: PRT
<213> ORGANISM: frog and mouse

<400> SEQUENCE: 5

Ser Lys Arg Ser Cys Ser Val Pro Glu Gly Met Val Cys Lys
1               5                   10

<210> SEQ ID NO 6
<211> LENGTH: 8
<212> TYPE: PRT
<213> ORGANISM: frog and mouse

<400> SEQUENCE: 6

Leu Arg Trp Arg Cys Gln Arg Arg
1               5

<210> SEQ ID NO 7
<211> LENGTH: 8
<212> TYPE: PRT
<213> ORGANISM: frog and mouse

<400> SEQUENCE: 7

Ile Ser Glu Cys Lys Cys Ser Cys
1               5

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:oligonucleotide

<400> SEQUENCE: 8
gactcgagtc gacatcgcag atgtggctgt ggtcac                                 36

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence:oligonucleotide
```

<400> SEQUENCE: 9
ccaagcttct agaattcgca ggaacactta cactcgg    37

<210> SEQ ID NO 10
<211> LENGTH: 1180
<212> TYPE: DNA
<213> ORGANISM: mouse
<220> FEATURE:
<221> NAME/KEY: CDS
<222> LOCATION: (421)..(1116)
<220> FEATURE:
<221> NAME/KEY: modified_base
<222> LOCATION: (16)
<223> OTHER INFORMATION: n=a, c, g, or t
<220> FEATURE:
<221> NAME/KEY: modified_base
<222> LOCATION: (235)
<223> OTHER INFORMATION: n=a, c, g, or t

<400> SEQUENCE: 10

| | |
|---|---:|
| taactcactc attagncacc ccagccttac actttatgct tccggctcgt atgttgtgtg | 60 |
| gaattgtgag cggataacaa tttcacacag gaaacagcta tgaccatgat tacgccaagc | 120 |
| tcgaaattaa ccctcactaa agggaacaaa agctggagct ccaccgcggt ggcggccgcc | 180 |
| ttcccaagta gagcggcggg ggggaattgc gaccaactcg tgcgcgtctt ctgcnccgcg | 240 |
| gcgggagccg cgcgctgcgcg aacggctctc ctcgcagctc atgctgcctg ccctgcgcct | 300 |
| gctcagcctc gggtgagcca cctccggagg gaccggggag cgcggcagcg ccgcggactc | 360 |
| ggcgtgctct cctccgggga cgcgggacga agaggcagcc ccggggcgcg cgcgggaggc | 420 |

```
atg gag cgc tgc ccc agc ctg ggg gtc acc ctc tac gcc ctg gtg gtg    468
Met Glu Arg Cys Pro Ser Leu Gly Val Thr Leu Tyr Ala Leu Val Val
  1               5                  10                  15 gtc ctg ggg ctg cgg gca gca cca gcc ggc ggc cag cac tat cta cac    516
Val Leu Gly Leu Arg Ala Ala Pro Ala Gly Gly Gln His Tyr Leu His
             20                  25                  30 atc cgc cca gca ccc agc gac aac ctg ccc ttg gtg gac ctc atc gaa    564
Ile Arg Pro Ala Pro Ser Asp Asn Leu Pro Leu Val Asp Leu Ile Glu
         35                  40                  45 cat cca gac cct atc ttt gac cct aag gag aag gat ctg aac gag acg    612
His Pro Asp Pro Ile Phe Asp Pro Lys Glu Lys Asp Leu Asn Glu Thr
     50                  55                  60 ctg ctg cgc tcg ctg ctc ggg ggc cac tac gac ccg ggc ttt atg gcc    660
Leu Leu Arg Ser Leu Leu Gly Gly His Tyr Asp Pro Gly Phe Met Ala
 65                  70                  75                  80 act tcg ccc cca gag gac cga ccc gga ggg ggc ggg gga ccg gct gga    708
Thr Ser Pro Pro Glu Asp Arg Pro Gly Gly Gly Gly Gly Pro Ala Gly
                 85                  90                  95 ggt gcc gag gac ctg gcg gag ctg gac cag ctg ctg cgg cag cgg ccg    756
Gly Ala Glu Asp Leu Ala Glu Leu Asp Gln Leu Leu Arg Gln Arg Pro
            100                 105                 110 tcg ggg gcc atg ccg agc gag atc aaa ggg ctg gag ttc tcc gag ggc    804
Ser Gly Ala Met Pro Ser Glu Ile Lys Gly Leu Glu Phe Ser Glu Gly
        115                 120                 125 ttg gcc caa ggc aag aaa cag cgc ctg agc aag aag ctg agg agg aag    852
Leu Ala Gln Gly Lys Lys Gln Arg Leu Ser Lys Lys Leu Arg Arg Lys
    130                 135                 140 tta cag atg tgg ctg tgg tca cag acc ttc tgc ccg gtg ctg tac gcg    900
Leu Gln Met Trp Leu Trp Ser Gln Thr Phe Cys Pro Val Leu Tyr Ala
145                 150                 155                 160 tgg aat gac cta ggc agc cgc ttt tgg cca cgc tac gtg aag gtg ggc    948
Trp Asn Asp Leu Gly Ser Arg Phe Trp Pro Arg Tyr Val Lys Val Gly
```

```
Trp Asn Asp Leu Gly Ser Arg Phe Trp Pro Arg Tyr Val Lys Val Gly
            165                 170                 175 agc tgc ttc agc aag cgc tcc tgc tct gtg ccc gag ggc atg gtg tgt      996
Ser Cys Phe Ser Lys Arg Ser Cys Ser Val Pro Glu Gly Met Val Cys
        180                 185                 190 aag cca tcc aag tct gtg cac ctc acg gtg ctg cgg tgg cgc tgt cag     1044
Lys Pro Ser Lys Ser Val His Leu Thr Val Leu Arg Trp Arg Cys Gln
    195                 200                 205 cgg cgc ggg ggt cag cgc tgc ggc tgg att ccc atc cag tac ccc atc     1092
Arg Arg Gly Gly Gln Arg Cys Gly Trp Ile Pro Ile Gln Tyr Pro Ile
210                 215                 220 att tcc gag tgt aag tgt tcc tgc tagaactcgg gggggcccc tgcccgcgcc     1146
Ile Ser Glu Cys Lys Cys Ser Cys
225                 230 cagacacttg atggatcccc cgggctgaga tttt                                1180
```

<210> SEQ ID NO 11
<211> LENGTH: 232
<212> TYPE: PRT
<213> ORGANISM: mouse
<400> SEQUENCE: 11

```
Met Glu Arg Cys Pro Ser Leu Gly Val Thr Leu Tyr Ala Leu Val Val
  1               5                  10                  15

Val Leu Gly Leu Arg Ala Ala Pro Ala Gly Gly Gln His Tyr Leu His
                 20                  25                  30

Ile Arg Pro Ala Pro Ser Asp Asn Leu Pro Leu Val Asp Leu Ile Glu
             35                  40                  45

His Pro Asp Pro Ile Phe Asp Pro Lys Glu Lys Asp Leu Asn Glu Thr
         50                  55                  60

Leu Leu Arg Ser Leu Leu Gly Gly His Tyr Asp Pro Gly Phe Met Ala
 65                  70                  75                  80

Thr Ser Pro Pro Glu Asp Arg Pro Gly Gly Gly Gly Pro Ala Gly
                 85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
        115                 120                 125

Leu Ala Gln Gly Lys Lys Gln Arg Leu Ser Lys Lys Leu Arg Arg Lys
130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
        195                 200                 205

Arg Arg Gly Gly Gln Arg Cys Gly Trp Ile Pro Ile Gln Tyr Pro Ile
    210                 215                 220

Ile Ser Glu Cys Lys Cys Ser Cys
225                 230
```

<210> SEQ ID NO 12
<211> LENGTH: 18
<212> TYPE: DNA
<213> ORGANISM: Artificial Sequence

```
<220> FEATURE:
<223> OTHER INFORMATION: Description of Artificial Sequence:primer
<220> FEATURE:
<221> NAME/KEY: modified_base
<222> LOCATION: (6)
<223> OTHER INFORMATION: n=a, c, g, or t
<220> FEATURE:
<221> NAME/KEY: modified_base
<222> LOCATION: (15)
<223> OTHER INFORMATION: n=a, c, g, or t
<220> FEATURE:
<221> NAME/KEY: modified_base
<222> LOCATION: (18)
<223> OTHER INFORMATION: n=a, c, g, or t

<400> SEQUENCE: 12
caracnttyt gyccngtn                                              18

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:primer
<220> FEATURE:
<221> NAME/KEY: modified_base
<222> LOCATION: (9)
<223> OTHER INFORMATION: n=a, c, g, or t
<220> FEATURE:
<221> NAME/KEY: modified_base
<222> LOCATION: (12)
<223> OTHER INFORMATION: n=a, c, g, or t
<220> FEATURE:
<221> NAME/KEY: modified_base
<222> LOCATION: (18)
<223> OTHER INFORMATION: n=a, c, g, or t
<220> FEATURE:
<221> NAME/KEY: modified_base
<222> LOCATION: (24)
<223> OTHER INFORMATION: n=a, c, g, or t

<400> SEQUENCE: 13
ttytggccnm gntaygtnaa rgtngg                                     26

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:primer
<220> FEATURE:
<221> NAME/KEY: modified_base
<222> LOCATION: (3)
<223> OTHER INFORMATION: n=a, c, g, or t
<220> FEATURE:
<221> NAME/KEY: modified_base
<222> LOCATION: (9)
<223> OTHER INFORMATION: n=a, c, g, or t
<220> FEATURE:
<221> NAME/KEY: modified_base
<222> LOCATION: (15)
<223> OTHER INFORMATION: n=a, c, g, or t

<400> SEQUENCE: 14
ccngarggna tggtntg                                               17

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:primer
<220> FEATURE:
```

```
<221> NAME/KEY: modified_base
<222> LOCATION: (3)
<223> OTHER INFORMATION: n=a, c, g, or t

<400> SEQUENCE: 15
canswrcayt trcaytc                                                17

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:primer
<220> FEATURE:
<221> NAME/KEY: modified_base
<222> LOCATION: (3)
<223> OTHER INFORMATION: n=a, c, g, or t
<220> FEATURE:
<221> NAME/KEY: modified_base
<222> LOCATION: (9)
<223> OTHER INFORMATION: n=a, c, g, or t
<220> FEATURE:
<221> NAME/KEY: modified_base
<222> LOCATION: (15)
<223> OTHER INFORMATION: n=a, c, g, or t

<400> SEQUENCE: 16
canaccatnc cytcngg                                                17

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence:primer
<220> FEATURE:
<221> NAME/KEY: modified_base
<222> LOCATION: (3)
<223> OTHER INFORMATION: n=a, c, g, or t
<220> FEATURE:
<221> NAME/KEY: modified_base
<222> LOCATION: (12)
<223> OTHER INFORMATION: n=a, c, g, or t

<400> SEQUENCE: 17
cknckytgrc anckcca                                                17

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:oligonucleotide

<400> SEQUENCE: 18
cagatgtggc tgtggtca                                               18

<210> SEQ ID NO 19
<211> LENGTH: 6
<212> TYPE: PRT
<213> ORGANISM: mouse

<400> SEQUENCE: 19

Gln Met Trp Leu Trp Ser
  1               5

<210> SEQ ID NO 20
<211> LENGTH: 18
<212> TYPE: DNA
```

```
<213> ORGANISM: Artificial Sequence
<220> FEATURE:
<223> OTHER INFORMATION: Description of Artificial Sequence:oligonucleotide

<400> SEQUENCE: 20
gcaggaacac ttacactc                                                        18

<210> SEQ ID NO 21
<211> LENGTH: 6
<212> TYPE: PRT
<213> ORGANISM: mouse

<400> SEQUENCE: 21

Glu Cys Lys Cys Ser Cys
 1               5

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:oligonucleotide
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i

<400> SEQUENCE: 22
garggnatgg tntgyaarcc                                                      20

<210> SEQ ID NO 23
<211> LENGTH: 449
<212> TYPE: PRT
<213> ORGANISM: human

<400> SEQUENCE: 23
```

| | | | | | | | | | | | | | | | |
|---|---|---|---|---|---|---|---|---|---|---|---|---|---|---|---|
| Met | Glu | Arg | Cys | Pro | Ser | Leu | Gly | Val | Thr | Leu | Tyr | Ala | Leu | Val | Val |
| 1 | | | | 5 | | | | | 10 | | | | | 15 | |
| Val | Leu | Gly | Leu | Arg | Ala | Thr | Pro | Ala | Gly | Gly | Gln | His | Tyr | Leu | His |
| | | | 20 | | | | | 25 | | | | | 30 | | |
| Ile | Arg | Pro | Ala | Pro | Ser | Asp | Asn | Leu | Pro | Leu | Val | Asp | Leu | Ile | Glu |
| | | 35 | | | | | 40 | | | | | 45 | | | |
| His | Pro | Asp | Pro | Ile | Phe | Asp | Pro | Lys | Glu | Lys | Asp | Leu | Asn | Glu | Thr |
| | 50 | | | | | 55 | | | | | 60 | | | | |
| Leu | Leu | Arg | Ser | Leu | Leu | Gly | Gly | His | Tyr | Asp | Pro | Gly | Phe | Met | Ala |
| 65 | | | | | 70 | | | | | 75 | | | | | 80 |
| Thr | Ser | Pro | Pro | Glu | Asp | Arg | Pro | Gly | Gly | Gly | Gly | Ala | Ala | Gly |
| | | | | 85 | | | | | 90 | | | | | 95 | |
| Gly | Ala | Glu | Asp | Leu | Ala | Glu | Leu | Asp | Gln | Leu | Leu | Arg | Gln | Arg | Pro |
| | | | 100 | | | | | 105 | | | | | 110 | | |
| Ser | Gly | Ala | Met | Pro | Ser | Glu | Ile | Lys | Gly | Leu | Glu | Phe | Ser | Glu | Gly |
| | | 115 | | | | | 120 | | | | | 125 | | | |
| Leu | Ala | Gln | Gly | Leu | Gln | Met | Trp | Leu | Trp | Ser | Gln | Thr | Phe | Cys | Pro |
| | 130 | | | | | 135 | | | | | 140 | | | | |
| Val | Leu | Tyr | Ala | Trp | Asn | Asp | Leu | Gly | Ser | Arg | Phe | Trp | Pro | Arg | Tyr |
| 145 | | | | | 150 | | | | | 155 | | | | | 160 |
| Val | Lys | Val | Gly | Ser | Cys | Phe | Ser | Lys | Arg | Ser | Cys | Ser | Val | Pro | Glu |
| | | | | 165 | | | | | 170 | | | | | 175 | |

-continued

```
Gly Met Val Cys Lys Pro Ser Lys Ser Val His Leu Thr Val Leu Arg
            180                 185                 190

Trp Arg Cys Gln Arg Arg Gly Gly Gln Arg Cys Gly Trp Ile Pro Ile
        195                 200                 205

Gln Tyr Pro Ile Ile Ser Glu Cys Lys Cys Ser Cys Ser Gly Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

We claim:

1. A variant of the human noggin polypeptide shown in SEQ ID NO: 2, wherein said variant differs from SEQ ID NO: 2 by a deletion comprising amino acid residues 138–144, and wherein said variant has the biological activities of the human noggin of SEQ ID NO: 2.

2. A composition comprising the variant of claim 1 and a pharmaceutical carrier.

3. A variant of the human noggin polypeptide shown in SEQ ID NO: 2, wherein said variant differs from SEQ ID NO: 2 by a deletion comprising amino acid residues 133–144, and wherein said variant has the biological activities of the human noggin of SEQ ID NO: 2.

4. A composition comprising the variant of claim 3 and a pharmaceutical carrier.

5. A variant of the human noggin polypeptide shown in SEQ ID NO: 2, wherein said variant differs from SEQ ID NO: 2 by a deletion comprising amino acid residues 139–144 and wherein said variant has the biological activities of the human noggin of SEQ ID NO: 2.

6. A composition comprising the variant of claim 5 and a pharmaceutical carrier.

* * * * *